United States Patent [19]

Chen et al.

[11] Patent Number: 6,075,130
[45] Date of Patent: Jun. 13, 2000

[54] ION BINDING COMPOUNDS, RADIONUCLIDE COMPLEXES, METHODS OF MAKING RADIONUCLIDE COMPLEXES, METHODS OF EXTRACTING RADIONUCLIDES, AND METHODS OF DELIVERING RADIONUCLIDES TO TARGET LOCATIONS

[75] Inventors: Xiaoyuan Chen, Syracuse, N.Y.; Chien M. Wai, Moscow, Id.; Darrell R. Fisher, Richland, Wash.

[73] Assignees: Battelle Memorial Institute, Richland, Wash.; Idaho Research Foundation, Inc., Moscow, Id.

[21] Appl. No.: 09/191,290

[22] Filed: Nov. 10, 1998

Related U.S. Application Data

[63] Continuation of application No. 08/968,996, Nov. 12, 1997.
[51] Int. Cl.[7] .................................................. C07F 5/02
[52] U.S. Cl. .............................. 534/10; 534/11; 534/15; 534/13; 423/9
[58] Field of Search .................................. 424/1.11, 1.37, 424/1.49, 1.65, 1.69, 9.1, 1.81; 534/7, 10–16; 549/347, 348, 349, 350, 352; 423/9

[56] References Cited

U.S. PATENT DOCUMENTS

| | | | |
|---|---|---|---|
| 5,205,946 | 4/1993 | Cook et al. | 252/25 |
| 5,210,216 | 5/1993 | Harris et al. | 548/518 |
| 5,453,220 | 9/1995 | Swager et al. | 252/582 |
| 5,607,591 | 3/1997 | Dozol et al. | 210/638 |
| 5,622,687 | 4/1997 | Krishnan et al. | 424/9.33 |
| 5,866,087 | 2/1999 | Dozol et al. | 423/9 |

FOREIGN PATENT DOCUMENTS

| | | |
|---|---|---|
| 9424138 | 10/1994 | WIPO . |
| 9623800 | 8/1996 | WIPO . |

OTHER PUBLICATIONS

Johann et al, J. Chem. Soc. Perkin Trans, 2, No. 6, pp. 1183–1192, "Solvent vs. Counterion acceleration of enantioseletive carbo and hetero Dielc—Act Alder reactions", 1997.

Sabbatini et al, Inurganico Chimica Acta, 25–2, pp. 19–24, "Luminescence of Eu 3t and Tb3t complexes of a new macrobicycle ligands derived from p–tert–butyl calix[4]avene", 1996.

Sabbatani et al, J. Chem. Soc. Chem. Commun. pp. 878–879, Encapsulation of Lanthanide Ions in Calixarene Receptors. A Strongly Luminescent terbium 3t complex, 1990.

Chang et al, J. Chem. Soc. Perkin Transl, pp. 211–214, "New Metal Cation—Selective Ionophores Derived from Calixarenes. Their Synthesis and Ion–Binding Properties", 1986.

Dozol et al, Value Adding Solvent Extraction, [Pap. ISec '96], vol. 2, pp. 1333–1338, "Extraction and Transport of Radioactive Cations through S. C.M.S with functionalized Calixarenes", 1996.

Seangproserakij, J. Org. Chem, 1994, 59, pp. 1741–1744, "Schoff Base p–tert–butylcalix[4]arenes. Synthesis and Metal Ion Complexation", 1994.

Hampton et al, Inorganic Chem, 36, pp. 2956–2959, "Selective Binding of Trivalent Metals by Hexahomotrioxacalix[3]arene Macromolecules: Determination of Metal binding Constants and metal Transport Studies", 1997.

Harrowfield et al, J. Chem. Soc. Dalton Trans, pp. 976–985, "Actinide complexes of the calixarenes. Part I—Synthesis and crystal structures of bis(homo–oxa)–p–tert–betycalix[4]arene and it uranyl ion complex", 1991.

*Primary Examiner*—Jose' G. Dees
*Assistant Examiner*—Dameron Jones
*Attorney, Agent, or Firm*—Wells, St. John, Roberts, Gregory & Matkin P.S.

[57] ABSTRACT

The invention pertains to compounds for binding lanthanide ions and actinide ions. The invention further pertains to compounds for binding radionuclides, and to methods of making radionuclide complexes. Also, the invention pertains to methods of extracting radionuclides. Additionally, the invention pertains to methods of delivering radionuclides to target locations. In one aspect, the invention includes a compound comprising: a) a calix[n]arene group, wherein n is an integer greater than 3, the calix[n]arene group comprising an upper rim and a lower rim; b) at least one ionizable group attached to the lower rim; and c) an ion selected from the group consisting of lanthanide and actinide elements bound to the ionizable group. In another aspect, the invention includes a method of extracting a radionuclide, comprising: a) providing a sample comprising a radionuclide; b) providing a calix[n]arene compound in contact with the sample, wherein n is an integer greater than 3; and c) extracting radionuclide from the sample into the calix[n]arene compound. In yet another aspect, the invention includes a method of delivering a radionuclide to a target location, comprising: a) providing a calix[n]arene compound, wherein n is an integer greater than 3, the calix[n]arene compound comprising at least one ionizable group; b) providing a radionuclide bound to the calix[n]arene compound; and c) providing an antibody attached to the calix[n]arene compound, the antibody being specific for a material found at the target location.

38 Claims, 16 Drawing Sheets

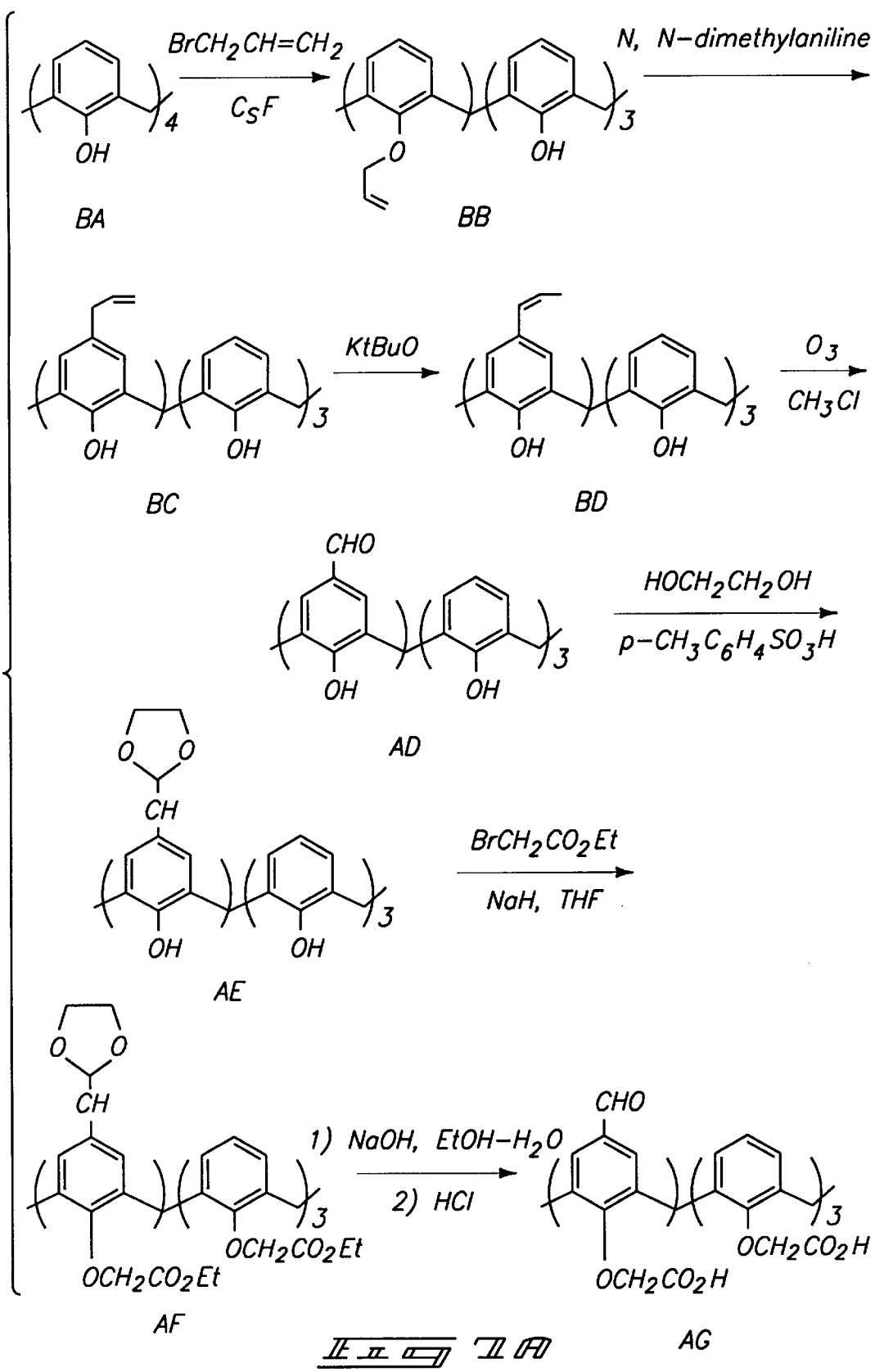

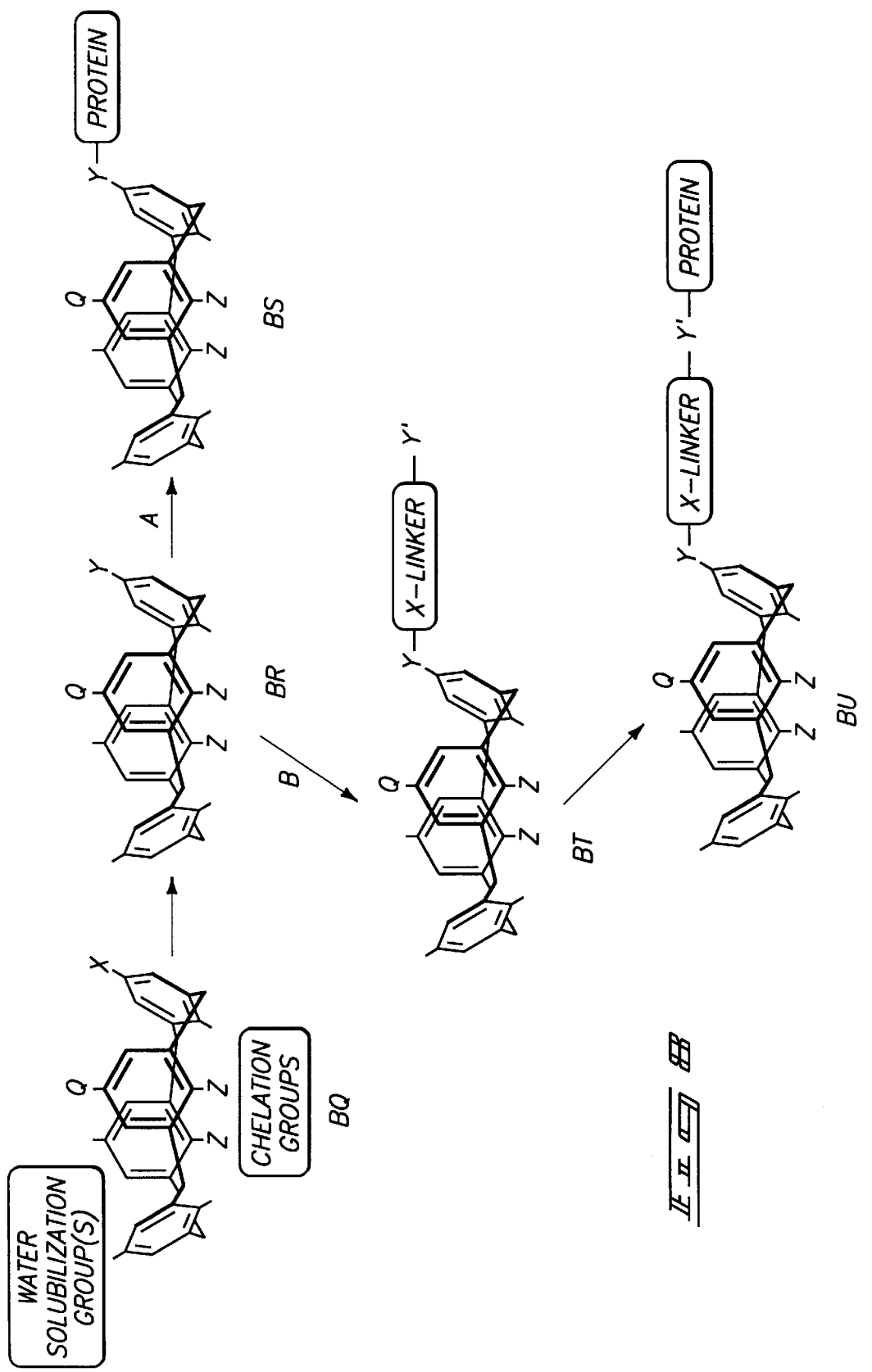

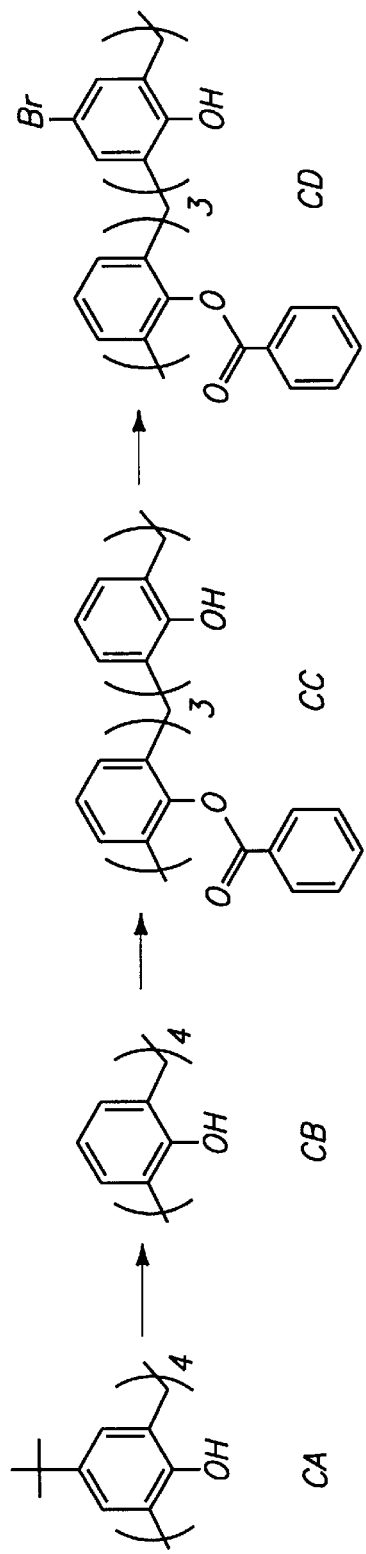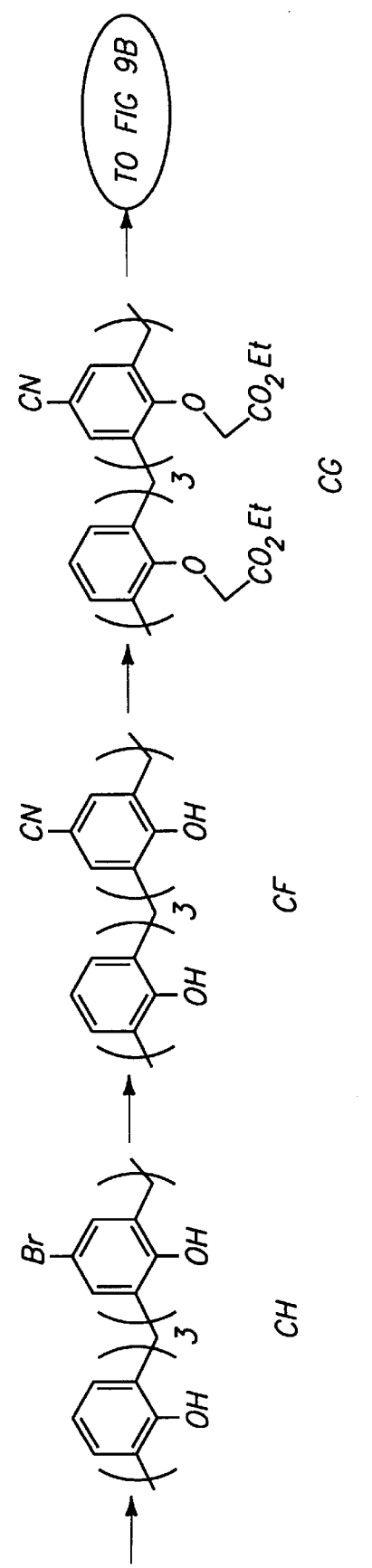
FIG 9A

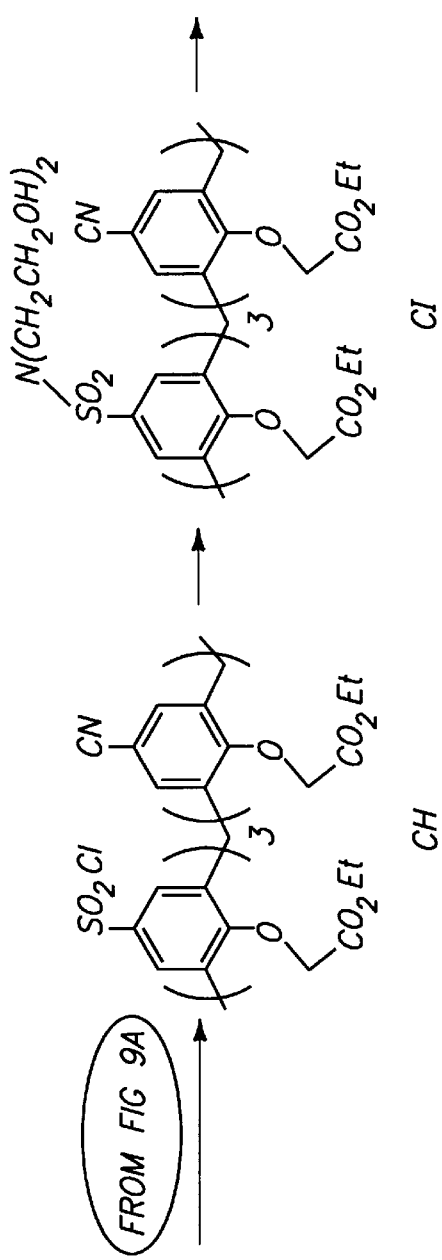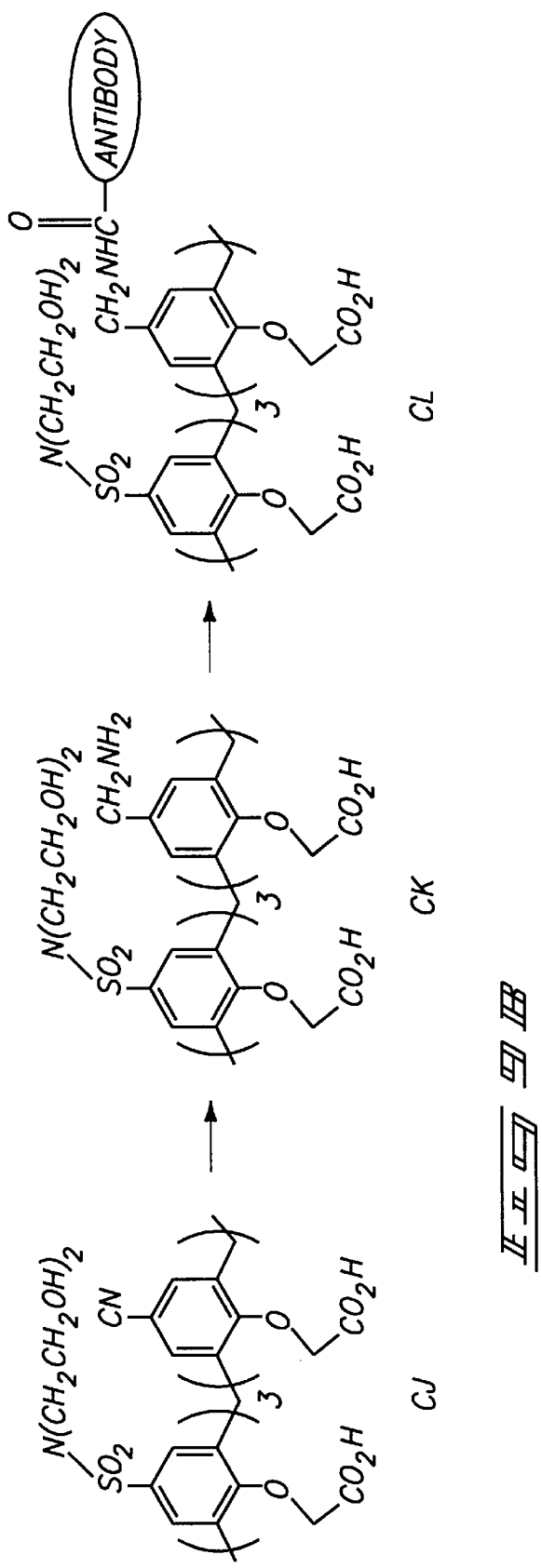
FIG. 9B

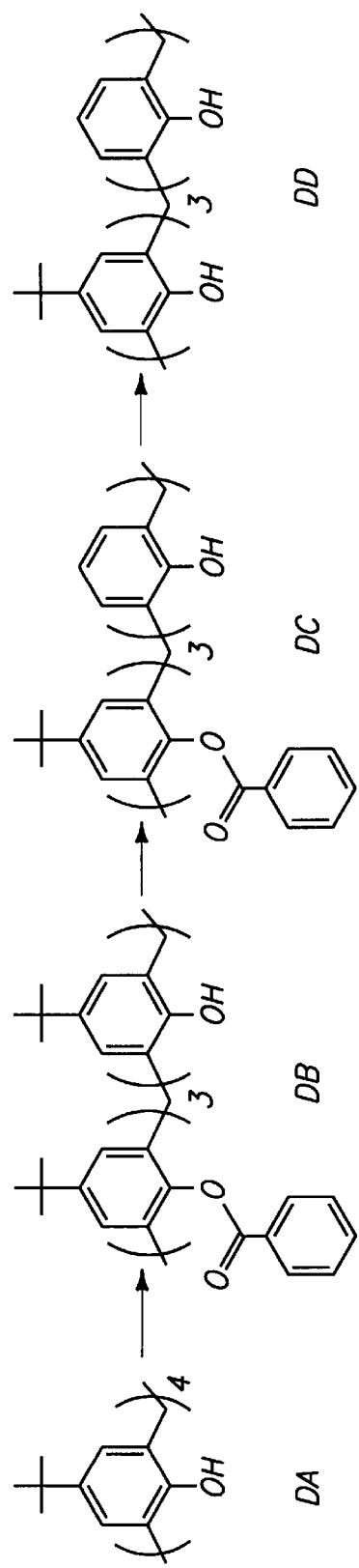

ION BINDING COMPOUNDS, RADIONUCLIDE COMPLEXES, METHODS OF MAKING RADIONUCLIDE COMPLEXES, METHODS OF EXTRACTING RADIONUCLIDES, AND METHODS OF DELIVERING RADIONUCLIDES TO TARGET LOCATIONS

RELATED PATENT DATA

This patent resulted from a continuation-in-part of U.S. patent application Ser. No. 08/968,996, filed on Nov. 12, 1997.

This invention was made with Government support under Contract DE-AC06 76RLO 1830 awarded by the U.S. Department of Energy. The Government has certain rights in the invention.

TECHNICAL FIELD

The invention pertains to compounds for binding lanthanide ions and actinide ions. The invention further pertains to compounds for binding radionuclides, and to methods of making radionuclide complexes. Also, the invention pertains to methods of extracting radionuclides. Additionally, the invention pertains to methods of delivering radionuclides to target locations.

BACKGROUND OF THE INVENTION

Lanthanide elements and actinide elements have a number of industrial and medicinal uses. For purposes of interpreting this document and the claims that follow, the term "lanthanide element" is defined to encompass the elements La, Ce, Pr, Nd, Pm, Sm, Eu, Gd, Tb, Dy, Ho, Er, Tm, Yb, and Lu, and the term "actinide element" is defined to encompass the elements Ac, Th, Pa, U, Np, Pu, Am, Cm, Bk, Cf, Es, Fm, Md, No, Lr, Rf, and Ha.

The above-listed lanthanide and actinide elements can be used, for example, as imaging agents. For instance, the elements Tb and Eu are characterized by fluorescence and luminescence, and can be used as probes in biological systems. Yb also has spectroscopic characteristics that enable it to be a useful probe in biological systems.

A difficulty in utilizing the lanthanide or actinide elements as probes in biological systems is in localizing the elements to specific areas of a biological system which are to be probed. Accordingly, it would be desirable to bind lanthanide or actinide elements to a transport compound which would specifically transport the elements to a localized region of a biological system.

Another use of lanthanide and actinide ions is as cell toxicity agents. For example, $^{225}$Ac is a radioactive element which decays successively to Bi-209 by emission of four alpha particles. Alpha particles are lethal to cells when they traverse cell nuclei in close proximity to the radioactive source. Accordingly, $^{225}$Ac has utility for cancer treatment. A difficulty in utilizing $^{225}$Ac for cancer treatment is to localize the $^{225}$Ac within close proximity to cancer cells. Accordingly, it would be desirable to develop a transport compound that would specifically transport $^{225}$Ac to cancer cells in a biological system.

In recent years there has been an increased interest in the development of monoclonal antibodies that specifically target cancer cells and tumors. It is thought that such antibodies can be labeled with radionuclides and utilized to transport the radionuclides to cancer cells and tumors for utilization in radioimmunodiagnosis and radioimmunotherapy of cancer. The success of such approaches depends on development of bifunctional complexing agents that can bind a radionuclide strongly and selectively, and that can be further linked to antibodies. Accordingly, it would be desirable to develop such bifunctional complexing agents.

A recently discovered class of compounds known as calixarenes, or "molecular baskets", show potential for being able to tightly and selectively bind a number of different elements. Calixarenes are cyclic oligomers made up of phenolic units meta-linked by methylene bridges and possessing bowl-shaped cavities. To specify a size of a calixarene, one intercalates between brackets a number that represents the number of phenolic units constituting calixarene. Four formulaic representations of a prior art calix[4] arene are illustrated in FIG. 1 as "A", "B", "C" and "D". Each formulaic representation has several R-groups. The R-groups represent alkyl groups, such as t-butyl groups. In the formulaic representation labeled "C", it shown that a calixarene can be thought of as a compound containing an upper rim 10 and a lower rim 12. A plurality of hydroxyl groups of the calixarene are attached to lower rim 12.

Calixarenes are relatively easy to synthesize. For example, many calixarenes can be synthesized by a one-pot base-induced condensation of p-substituted phenol and formaldehyde.

SUMMARY OF THE INVENTION

In one aspect, the invention includes a compound which has a calix[n]arene group, wherein n is an integer greater than 3. The calix[n]arene group comprises an upper rim and a lower rim. The compound further has at least one ionizable group attached to the lower rim, and an ion selected from the group consisting of lanthanide and actinide elements bound to the ionizable group.

In another aspect, the invention includes a method of making a radionuclide complexing compound. A calix[n] arene compound is provided, wherein n is an integer greater than 3. The calix[n]arene compound comprises at least one phenolic hydroxyl group. The hydroxyl group is converted to an ester, and the ester is converted to an acid. A radionuclide is provided to be bound to the acid.

In yet another aspect, the invention includes a method of extracting a radionuclide. A sample comprising a radionuclide is provided. A calix[n]arene compound is provided in contact with the sample, wherein n is an integer greater than 3. Radionuclide is extracted from the sample and into the calix[n]arene compound.

In yet another aspect, the invention includes a method of delivering a radionuclide to a target location. A calix[n]arene compound is provided, wherein n is an integer greater than 3. The calix[n]arene compound includes at least one ionizable group. A radionuclide is bound to the calix[n]arene compound. An antibody specific for a material found at the target location is attached to the calix[n]arene compound.

BRIEF DESCRIPTION OF THE DRAWINGS

Preferred embodiments of the invention are described below with reference to the following accompanying drawings.

FIG. 8 illustrates a generalized reaction scheme for attaching proteins to compounds of the present invention.

FIGS. 9A and B illustrate a series of methods for linking antibodies and water solubilization groups with compounds of the present invention.

DETAILED DESCRIPTION OF THE PREFERRED EMBODIMENTS

This disclosure of the invention is submitted in furtherance of the constitutional purposes of the U.S. Patent Laws "to promote the progress of science and useful arts" (Article 1, Section 8).

Figure 1:
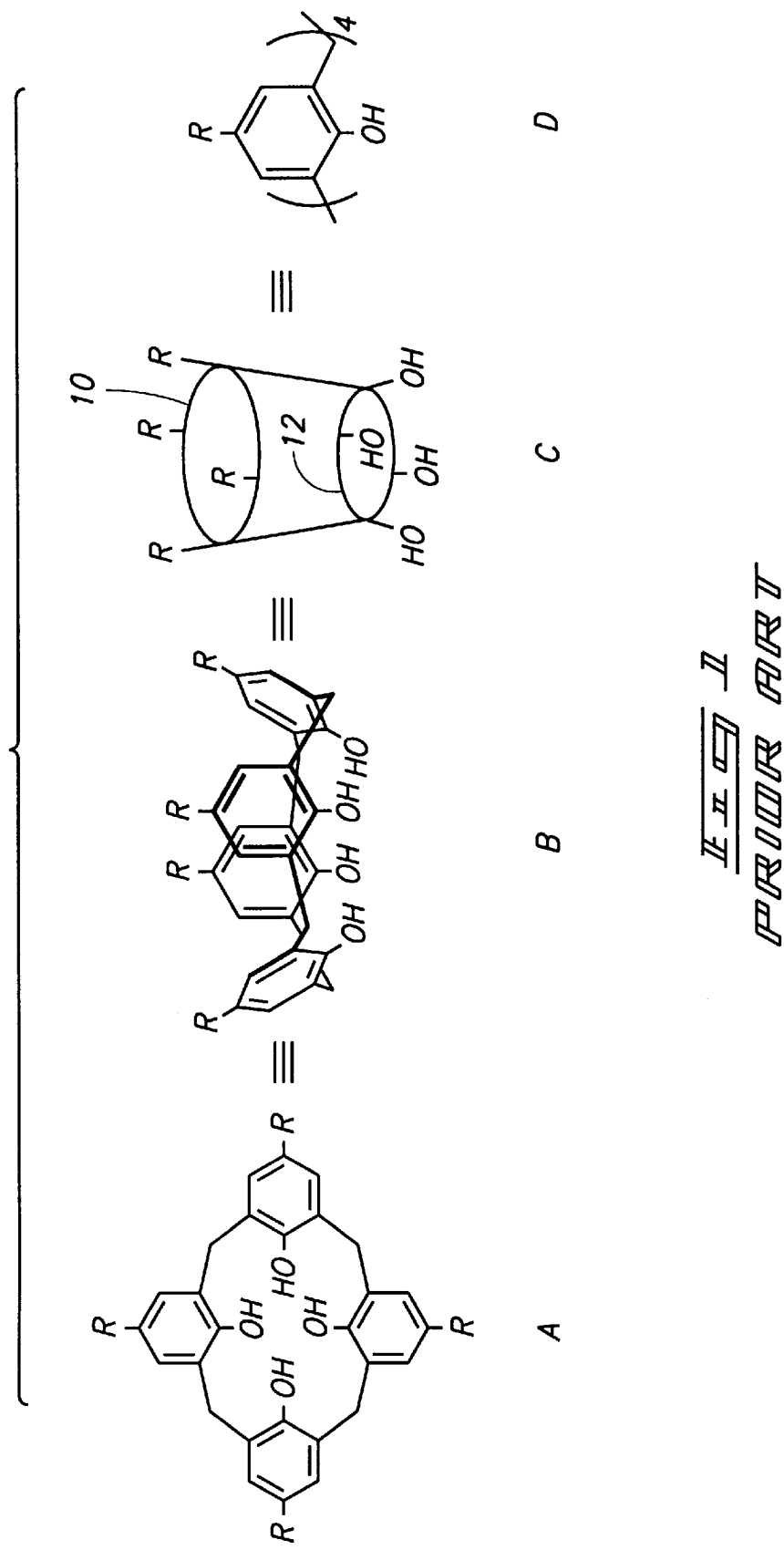
FIG. 1 illustrates four formulaic representations of a prior art calix[4]arene.

In a particular aspect, the invention encompasses compounds comprising calix[n]arene groups having at least one ionizable group attached to a lower rim 12 (shown in FIG. 1) of the calix[n]arene group, and having an ion selected from the group consisting of lanthanide and actinide elements bound to the ionizable group. The n in calix[n]arene preferably comprises an integer greater than 3 and less than 7. The ion can comprise, for example, $Ac^{3+}$, $Eu^{2+}$, $Tb^{4+}$, or $Yb^{2+}$.

Figure 2:
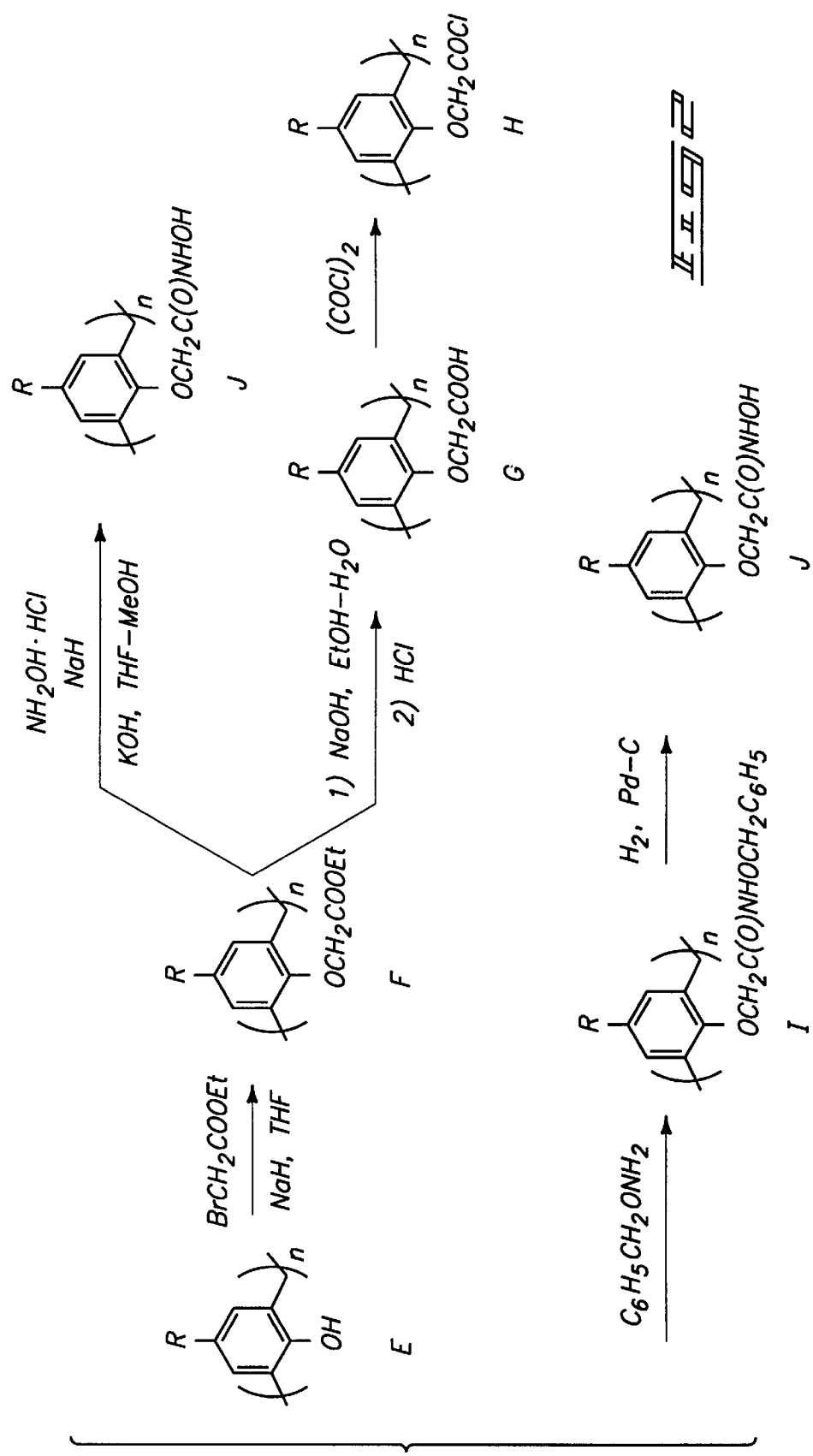
FIG. 2 illustrates two methods of synthesizing compounds of the present invention.

The ionizable group attached to the calix[n]arene can comprise, for example, one or more functional groups selected from the group consisting of carboxylic acid and hydroxamic acid. Methods for attaching carboxylic acid or hydroxamic acid to a lower rim 12 (shown in FIG. 1) of a calix[n]arene are described with reference to FIGS. 2–4. Referring first to FIG. 2, a synthesis starts with a calix[n]arene compound "E". Compound "E" comprises n aryl rings, wherein n is an integer greater than 3 and less than 7. For instance, n can be 4 or 6. Compound "E" further comprises n R-groups. The R-groups influence the solubility of compound "E" in various solvents. If the solvents are organic, the R-groups can include alkyl groups such as t-butyl, and can include H. If the solvent is water, the R-groups are preferably selected from a group consisting of $-SO_3H$, $-SO_2N(CH_2CH_2OH)_2$, $-N^+R_3$, polyethyleneoxy chains, $-SO_2NHCH_2C(O)N(CH_2CH_2OH)_3$, $-PO_3^-$, and other polar groups, to make compound "E" water soluble.

Compound "E" is reacted with $BrCH_2COOEt$ and sodium hydride in tetrahydrofuran (THF) to convert one or more phenolic hydroxyl groups of "E" into esters and to thereby form "F". More specifically, "F" is formed as follows. To a stirred solution of "E" (1 mmol) in dry THF (50 mL) is added sodium hydride (0.2 g, ca. 10 mmol) followed by ethyl bromoacetate (1.7 g, 10 mmol). The reaction mixture is refluxed under nitrogen overnight. Subsequently, the solvent is removed under reduced pressure to yield "F".

Compound "F" is reacted in sodium hydroxide, ethanol and water, followed by neutralization with HCl, to convert the esters to carboxylic acids and to thereby form "G". More specifically, "F" is converted to "G" as follows. To "F" (1 mmol in 30 ml of ethanol) is added 3N NaOH (20 ml), and the resulting mixture is refluxed for 24 hours. Most of the ethanol is then removed under reduced pressure to form a reduced solution. An excess of 2N HCl is added to the reduced solution to precipitate a white solid ("G"). The crude white solid is extracted with chloroform to remove inorganic salts. The resulting residue is recrystallized from ethanol-$H_2O$.

Compound "G" can be combined with a lanthanide or actinide ion to bind the ion with compound "G". Alternatively, compound "G" can be further reacted via the scheme in FIG. 2 to form a hydroxamic acid from the carboxylic acid. Specifically, compound "G" is reacted with $(COCl)_2$ to form acid chloride derivative "H". Compound "H" is then reacted with $C_6H_5CH_2ONH_2$ to form compound "I". Subsequently, compound "I" is reacted with $H_2$ using Pd—C as a catalyst to form the hydroxamic acid derivative "J". Alternatively, compound "J" can be produced by a one-pot reaction from compound "F" and hydroxylamine in a relatively low yield. Compound "J" can be combined with a lanthanide or actinide ion to bind the ion.

It is noted that a degree of derivatization of the calix[n]arenes of the present invention can be controlled by the basicity, amount of ethyl bromoacetate, and amount of different bases. Thus, compound "G" can comprise numerous partially derivatized and fully derivatized calix[n]arene carboxylic acid derivatives, including calix[4]arene-monocarboxylic acid, calix[4]arene-dicarboxylic acid, calix[4]arene-tricarboxylic acid, calix[4]arene-tetracarboxylic acid, calix[6]arene-monocarboxylic acid, calix[6]arene-dicarboxylic acid, calix[6]arene-tricarboxylic acid, calix[6]arene-tetracarboxylic acid, calix[6]arene-pentacarboxylic acid, and calix[6]arene-hexacarboxylic acid. Further, compound "J" can comprise numerous partially derivatized and fully derivatized calix[n]arene hydroxamic acid derivatives, including calix[4]arene-monohydroxamic acid, calix[4]arene-dihydroxamic acid, calix[4]arene-trihydroxamic acid, calix[4]arene-tetrahydroxamic acid, calix[6]arene-monohydroxamic acid, calix[6]arene-dihydroxamic acid, calix[6]arene-trihydroxamic acid, calix[6]arene-tetrahydroxamic acid, calix[6]arene-pentahydroxamic acid and calix[6]arene-hexahydroxamic acid.

Figure 3:
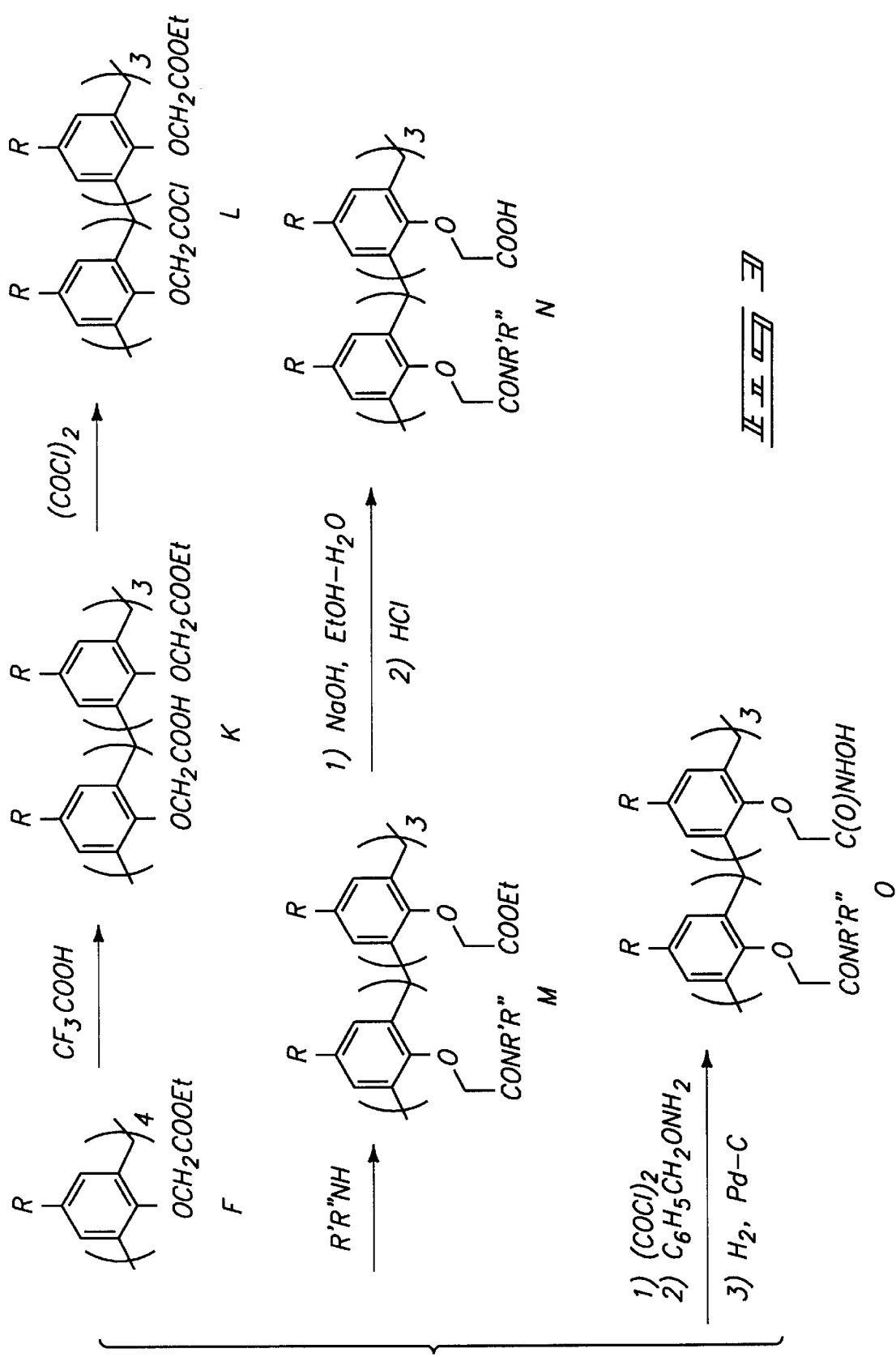
FIG. 3 illustrates a third method of synthesizing compounds of the present invention.

Alternate synthesis routes for forming hydroxamic acid derivatives and carboxylic acid derivatives of calix[n]arenes are illustrated in FIG. 3. The reaction sequence of FIG. 3 starts with compound "F" of FIG. 2. Compound "F" is reacted with $CF_3COOH$ to form compound "K". Compound "K" is then reacted with $(COCl)_2$ to form compound "L". Subsequently, compound "L" is reacted with R'R"NH to form "M". The R'-group comprises methyl or ethyl, and the R"-group comprises methyl or ethyl. The amide groups (such as CONR'R") generally have higher metal affinity than corresponding aryl esters. Compound "M" is reacted with sodium hydroxide in ethanol and water, followed by neutralization with hydrochloric acid, to form compound "N". Compound "N" is a carboxylic acid derivative of a calix[n]arene which can subsequently be bound to a lanthanide ion or an actinide ion. Alternatively, compound "N" can be reacted with $(COCl)_2$, followed by reaction with $C_6H_5CH_2ONH_2$, followed by reaction with hydrogen and Pd—C to form compound "O". Compound "O" is a hydroxamic acid derivative of a calix[n]arene which can subsequently be bound to a lanthanide ion or an actinide ion.

Although the reaction sequence of FIG. 3 is illustrated for a calix[4]arene, it is to be understood that the reaction sequence could also apply to other calix[n]arenes.

Figure 4:
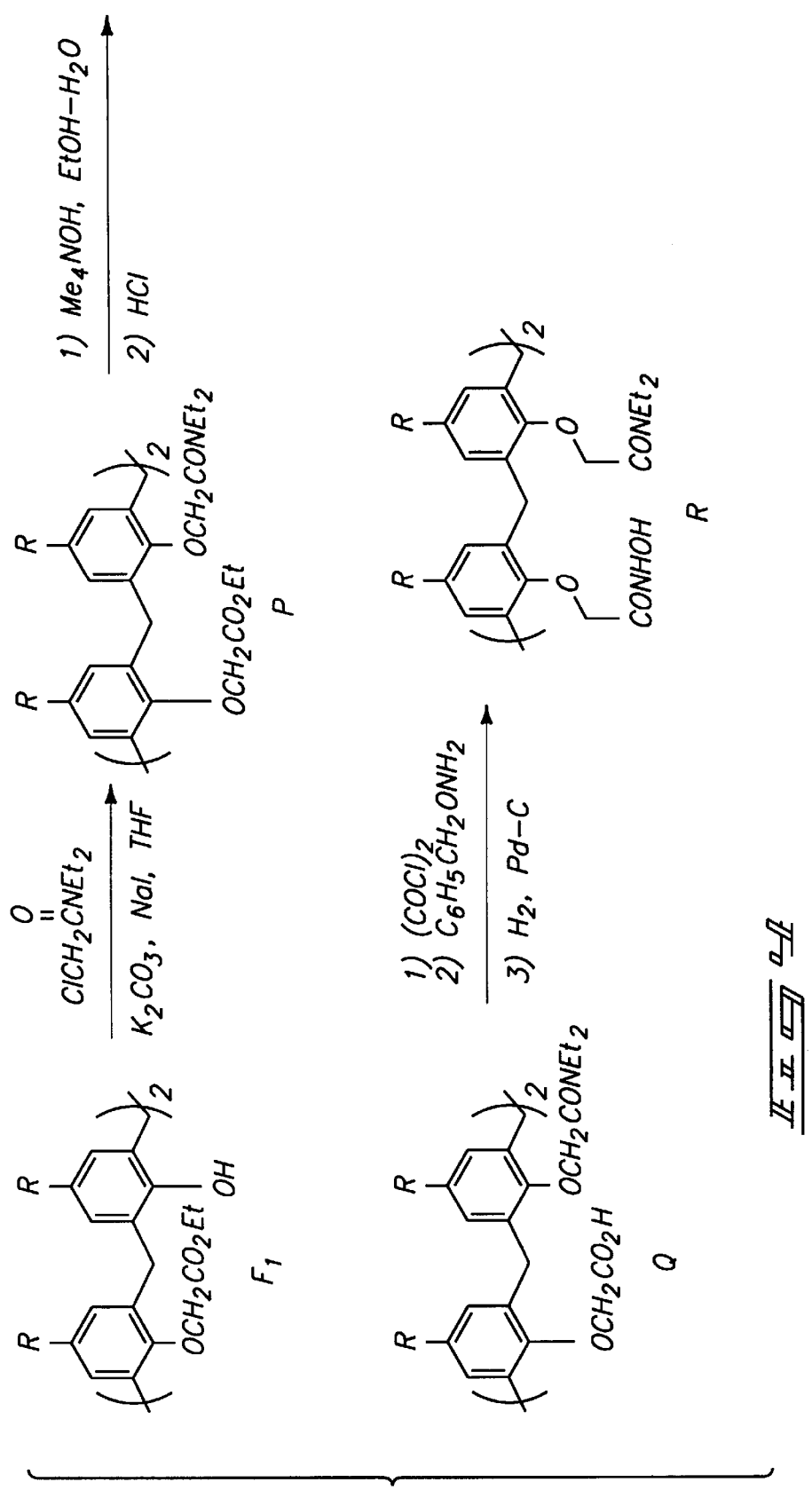
FIG. 4 illustrates a fourth method of synthesizing compounds of the present invention.

Another reaction sequence for forming hydroxamic acid derivatives and carboxylic acid derivatives of calix[n]arenes is illustrated in FIG. 4. The reaction sequence of FIG. 4 starts with compound "$F_1$", which is similar to compound "F" of FIG. 2. Compound "$F_1$" is reacted with $ClCH_2CONEt_2$, $K_2CO_3$ and NaI, in THF to form compound "P". Compound "P" is then reacted with $Me_4NOH$, EtOH and water, followed by neutralization with hydrochloric acid, to form compound "Q". Compound "Q" is a carboxylic acid derivative of a calix[n]arene which can then be bound to a lanthanide or actinide ion. Alternatively, compound "Q" can be reacted with $(COCl)_2$, followed by reaction with $C_6H_5CH_2ONH_2$, and followed by reaction with $H_2$ and Pd—C to form compound "R". Compound "R" is a hydroxamic acid derivative of a calix[n]arene can subsequently be bound to a lanthanide ion or an actinide ion.

The derivatized calix[n]arene compounds "G", "J", "N", "O", "Q", and "R" can be utilized for a number of applications. For example, the compounds can be utilized to selectively extract radionuclides from solutions comprising such radionuclides, such as radioactive waste. For instance, a calix[4]arene-dicarboxylic acid can be utilized to selectively extract $Ac^{3+}$ from samples comprising $Ac^{3+}$. After extraction of the radionuclide from the samples, the $Ac^{3+}$-calix[4]arene-dicarboxylic acid complex can be removed from the samples to clean the samples of radioactivity. The samples are then non-radioactive and can be disposed of by relatively low-cost procedures, rather than the high-cost procedures normally associated with radioactive waste disposal.

Another example use of the calix[n]arene compounds of the present invention is to deliver radionuclides to specific target locations. To utilize the compounds for such delivery of radionuclides, the compounds can be first joined to one or more chemicals specific to a target location. A class of chemicals known to have particular targeting abilities are antibodies. For instance, the monoclonal antibody referred to as B1-anti-CD20 (produced by Coulter Immunology, Inc.) is known to be specific for tumor cells.

As antibodies are proteins, the calix[n]arene compounds of the present invention can be linked to antibodies using conventional protein linking functional groups. Preferably, functional groups for linking proteins to the calix[n]arene compounds of the present invention are provided on upper rim 10 (shown in FIG. 1) of the calix[n]arene compounds. Example methods for forming such functional groups on an upper rim of a calix[n]arene compound are described with reference to FIGS. 5–7.

Figure 5:
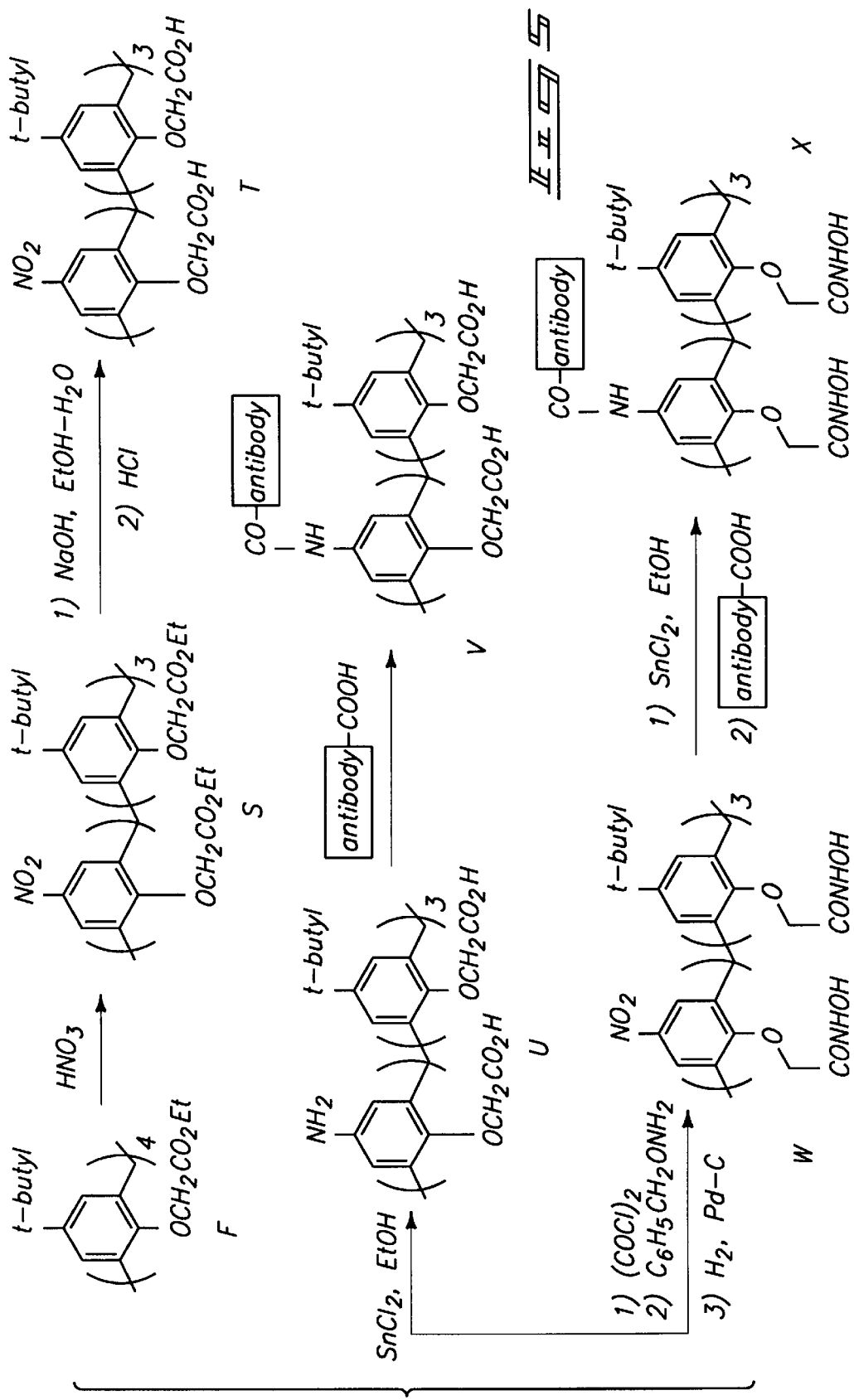
FIG. 5 illustrates a first series of methods of linking antibodies to compounds of the present invention.

Referring to FIG. 5, an amine linking group is formed on an upper rim of a calix[n]arene compound derivatized with tetracarboxylic acid or tetrahydroxamic acid on its lower rim. The synthesis shown in FIG. 5 begins with compound "F" of FIG. 2. Compound "F" is reacted with nitric acid to form compound "S". Compound "S" is reacted first with sodium hydroxide in ethanol and water, and subsequently with hydrochloric acid to form the calix[4]arene-tetracarboxylic acid derivative "T". Compound "T" can then be reacted by either of two alternative synthetic routes to form either the tetracarboxylic acid derivative "V" or the tetrahydroxamic acid derivative "X". Referring first to the synthesis of "V", compound "T" is reacted with $SnCl_2$ in ethanol to form "U". Compound "U" comprises an amine group. The amine group of "U" is reacted with a carboxylic acid group of a protein, such as an antibody, to form "V". Proteins contain carboxylic acid groups at their C terminus, as well as at side chains of various amino acids. Methods of forming peptide bonds between amine groups and carboxylic acid groups are known to persons of ordinary skill in the art. The calix[n]arene compound "U" can be bound to a radionuclide before attaching the compound to an antibody to form "V". Alternatively, "V" can be formed from "U" which is not bound to a radionuclide, and "V" can be subsequently bound to a radionuclide.

Referring next to the synthesis of compound "X", "T" is reacted with $(COCl)_2$, followed by $C_6H_5CH_2ONH_2$, followed by $H_2$ and Pd—C to form compound "W". Compound "W" is then reacted first with $SnCl_2$ in ethanol, and subsequently with a carboxylic acid group of an antibody to form compound "X". The calix[n]arene compound "W" can be bound to a radionuclide before attaching the compound to an antibody to form "X". Alternatively, "X" can be formed from "W" which is not bound to a radionuclide, and "X" can be subsequently bound to a radionuclide.

Figure 6:
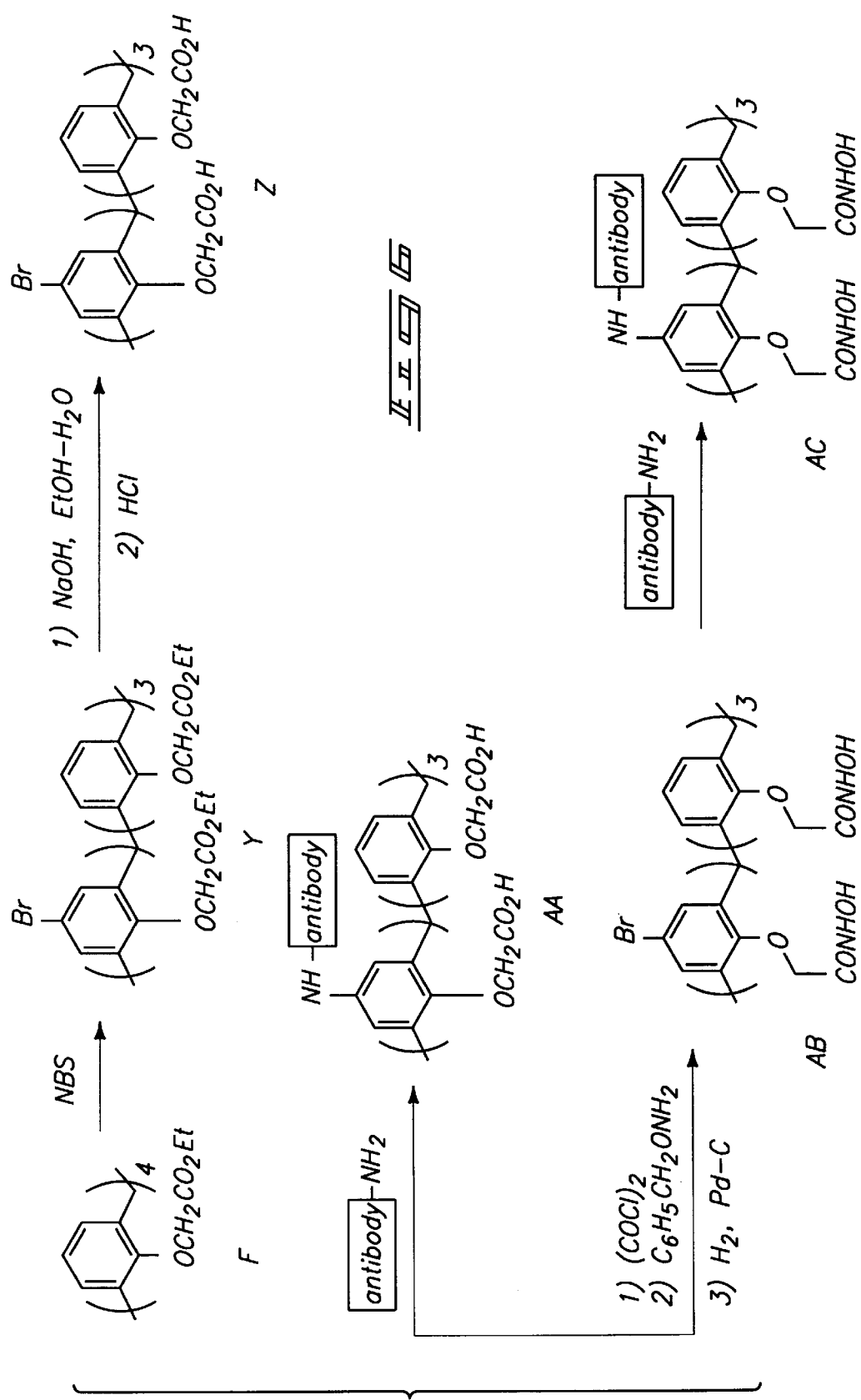
FIG. 6 illustrates a second series of methods of linking antibodies to compounds of the present invention.

Referring to FIG. 6, an alternate method of attaching an antibody to a calix[4]arene-tetracarboxylic acid or calix[4]arene-tetrahydroxamic acid is shown. The reaction scheme of FIG. 6 starts with compound "F" from FIG. 2, which is reacted with N-bromosuccinimide (NBS) to form the brominated compound "Y". Compound "Y" is then reacted with sodium hydroxide in ethanol and water, followed by neutralization with hydrochloric acid, to form "Z". Compound "Z" can then be reacted directly with an antibody to form the compound "AA". Alternatively, compound "Z" can be converted to a hydroxamic acid derivative "AB" prior to reaction with an antibody to form compound "AC". In reacting either compound "Z" or compound "AB" with an antibody, a bromine is displaced by an amino group of the antibody. Antibodies have amino groups at their N-terminus, as well as at the side chains of various amino acids. Methods of displacing bromine with amino groups are known to persons of ordinary skill in the art.

Figure 7B:
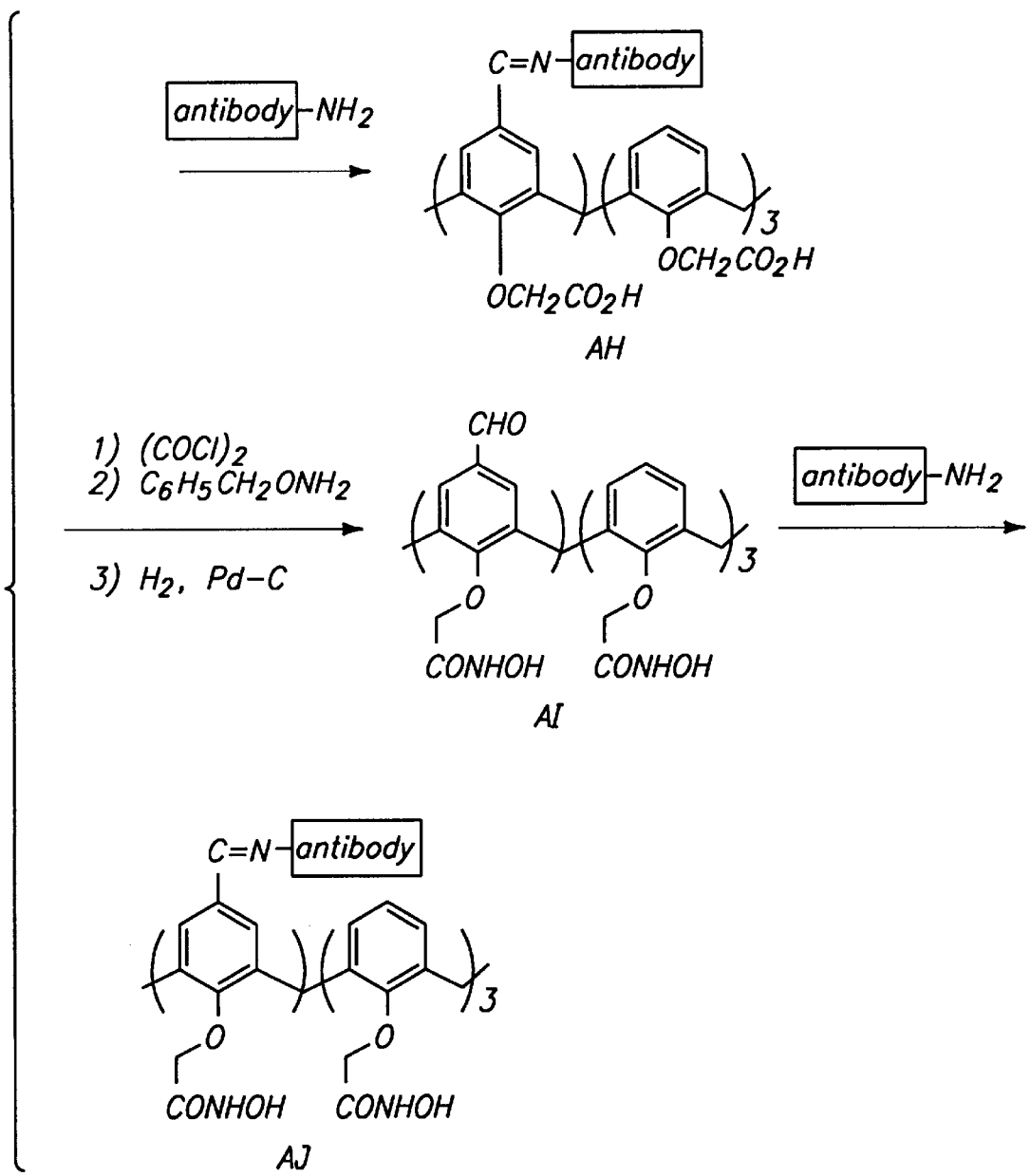
FIGS. 7A and B illustrate a third series of methods of linking antibodies to compounds of the present invention.

Referring to FIG. 7, another method for attaching an antibody to a calix[4]arene-tetracarboxylic acid or calix[4]arene-tetrahydroxamic acid is shown. The reaction scheme of FIG. 7 starts with a calix[4]arene compound "BA". Compound "BA" is converted to a monoallyl ether derivative (compound "BB") by reacting equivalent moles of "BA" and allyl bromide in the presence of a very weak base CsF. Claisen rearrangement of "BB" in refluxing N,N-dimethylaniline leads to mono-2-propenylcalix[4]arene (compound "BC"). Subsequent isomerization of the double bond with tBuOK converts "BC" to "BD". Ozonolysis of "BD" in $CHCl_3$ forms mono-carboxaldehyde-calix[4]arene (compound "AD"). Compound "AD" is reacted with $HOCH_2CH_2OH$ and $p-CH_3C_6H_4SO_3$ to form compound "AE", which is then reacted with $BrCH_2CO_2Et$, and sodium hydride in THF to form "AF". Compound "AF" is reacted with sodium hydroxide in ethanol and water, and subsequently neutralized with hydrochloric acid, to form "AG". Compound "AG" can be reacted with an antibody to form calix[4]arene-tetracarboxylic acid bound to the antibody (compound "AH"). Alternatively, compound "AG" can be reacted with $(COCl)_2$, followed by reaction with $C_6H_5CH_2ONH_2$, followed by reaction with hydrogen and Pd—C to form the tetrahydroxamic acid derivative "AI". Compound "AI" can then be reacted with an antibody to attach the antibody to the calix[4]arene-tetrahydroxamic acid and form "AJ". Regardless of which of the FIG. 7 reaction routes is chosen, an amino group of an antibody will react with an aldehyde of a calix[4]arene compound. Methods for reacting amino groups of proteins with aldehydes are known to persons of ordinary skill in the art.

In preferred aspects of the present invention, water solubilization groups are bound to calixarene compounds of the present invention to increase solubility of the compounds in aqueous solutions. Suitable water solubilization functional groups include, for example, sulfonates, nitrates, carboxylates, and ammonium ions. Water solubility of calixarene compounds of the present invention can be particularly important in applications wherein the compounds are bound to proteins (such as, for example, antibodies). If the calixarene compounds are insoluble, this can cause precipitation or aggregation of proteins associated with the compounds.

Some methods of binding proteins to calixarene compounds were described above with reference to FIGS. 5–7. Additional methods are described below with reference to FIGS. 8–10. Referring first to FIG. 8, such shows a general reaction scheme wherein a calixarene molecule "BQ" is provided to have a water solubilization group Q on its upper rim (10 of FIG. 1) and a pair of chelation groups Z on its lower rim (12 of FIG. 1). Chelation groups Z can comprise, for example, carboxylic acid and/or hydroxamic acid. It is to be understood that compound "BQ" is merely an exemplary compound. For instance, in other embodiments compound "BQ" could comprise more than one water solubilization group Q, and from one to four chelation groups Z.

In addition to the water solubilization group Q on the upper rim, compound "BQ" also comprises a component X on the upper rim. Component X will ultimately be utilized for attaching a protein to the calixarene of compound "BQ". An initial reaction is to convert component X to a functional group Y, and to thereby convert compound "BQ" to the illustrated compound "BR". Functional group Y is chosen to be either directly reactive with a protein, or to be reactive with a cross-linking reagent.

After the initial reaction, compound "BR" can proceed through one of two illustrated reaction pathways for linking a protein to the calixarene. A first reaction pathway (illustrated as pathway "A" in FIG. 8) comprises reacting Y reacted with a protein to form the compound "BS". Suitable functional groups Y for reaction with proteins are described above with reference to FIGS. 5–7. A second reaction pathway (illustrated as pathway "B" in FIG. 8) comprises initial linking of functional group Y with a cross-linking reagent, and subsequent reaction of the cross-linking reagent with a protein. More specifically, compound "BR" is reacted with a cross-linking reagent to form a reactive functional group Y' attached to the calixarene and to thereby form the molecule "BT". Y' is then reacted with a functional group on a protein to form the molecule "BU".

In the reaction sequences shown in FIG. 8, both the water solubilization group Q and the protein reactive group Y (or Y') are attached to an upper rim (10 of FIG. 1) of a calixarene compound. Such is a preferred orientation, as such can avoid interference of water solubilization group Q with chelating activity of chelation groups Z. A difficulty in providing water solubilization group Q at the top of a calixarene structure is that such can enable rotation of an aryl ring of a calixarene molecule about one of the bridging methylenes that connects the aryl ring with other aryl rings of the molecule. Typically, large, bulky groups (such as tertiary butyl groups) are provided on the upper rim of calixarene structures to restrict aryl groups from rotating about bridging methylenes. However, it is found that in methods of the present invention, provision of metal chelation structures at the bottoms (i.e., on the lower rim) of calixarene compounds can block rotation of aryl groups about bridging methylene groups. Accordingly, it is generally preferred to provide chelating groups on calixarene compounds of the present invention relatively early in synthetic reaction sequences for forming calixarene compounds of the present invention. The early incorporation of chelating groups Z onto calixarene compounds of the present invention may lead to difficulties in later steps of synthesis of calixarene compounds of the present invention, as the chelating functional groups may be reactive with components utilized in the later sequence steps. However, such difficulties can be overcome by protecting and de-protecting the chelating functional groups.

The functional group Y utilized in reaction pathway "A" (i.e., the group Y utilized for direct reaction with a protein) can comprise, for example, an activated carboxylate ester for reaction with amine groups on a protein. Exemplary activated carboxylate esters include, N-hydroxysuccinimidyl ester, N-hydroxyphthalimide esters, phenyl ester, p-nitrophenyl ester, tetrafluorophenyl ester, and pentafluorophenyl ester. Alternatively, Y can be a sulfhydryl reactive moiety, such as, for example, maleimides, alpha-halo acids, benzyl halides, and alkyl halides. In yet other alternative embodiments, Y can be reactive with oxidized carbohydrate or amino acid groups on a protein. In such alternative embodiments, Y can be an aldehyde or ketone reactive moiety, such as, for example, amines (which can be obtained through, for example, reductive amination) alkyl hydrazines, aryl hydrazines, acyl hydrazines, and alkoxylamines. In yet another alternative embodiment, Y can be reactive with carboxylates on a protein and can comprise, for example, an amine (wherein the conjugation can be facilitated by, for example, the use of a water solubilized carbodiimide).

In the reaction pathway "B" of FIG. 8, Y can be, for example, an amine group, sulfhydryl group, or hydrazine group. Utilization of a cross-linking reagent (pathway "B") can be preferred over direct reaction of a calixarene with a protein (pathway "A"), in that the cross-linking reagent can function as a spacer between a protein and the calixarene to alleviate steric interactions that could interfere with the calixarene's utilization in chelation processes. The cross-linking reagent attached to "Y" can be commercially or synthetically available, and can be homobifunctional or heterobifunctional. With homobifunctional cross-linking reagents, there are two identical reactive moieties on each end. A large excess of the homobifunctional cross-linking reagent must generally be used to avoid cross-linking between calixarenes. Homobifunctional cross-linking reagents include, but are not limited to, bismaleimidohexane (which is reactive with sulfhydryl groups), disuccinimidyl glutarate (which is reactive with amines), disuccinimidyl tartrate (reactive with amines), and dimethyl adipimidate (reactive with amines).

Heterobifunctional cross-linking reagents comprise two different reactive functionalities. Accordingly, selective reaction with "Y" can be achieved without cross-linking two calixarene moieties. Heterobifunctional cross-linking reagents are generally preferred. Exemplary heterobifunctional cross-linking reagents include molecules reactive with amines and sulfhydryl groups, such as, for example, N-maleimidobutyrloxysuccinimide ester and m-maleimidobenzoyl-N-hydroxysuccinimide ester.

Exemplary methods for attaching water solubilization groups and proteins to calixarene compounds of the present invention are shown in FIGS. 9 and 10. Referring first to FIGS. 9A and 9B, t-butylcalix[4]arene (compound "CA") is reacted with $AlCl_3$, phenol and toluene to convert "CA" (through Lewis acid catalyzed de-tert-butylation) to calix[4]arene (compound "CB"). The calix[4]arene is reacted with benzoyl chloride in pyridine to form 25, 26, 27-tribenzoyloxy-28-hydroxycalix[4]arene (compound "CC"). Compound "CC" is reacted with $Br_2$ in $CH_2Cl_2$ to form the illustrated compound "CD". Compound "CD" is reacted with NaOH in THF—EtOH—$H_2O$ to form the compound "CE". Compound "CE" is converted to cyanocalix[4]arene (compound "CF") with cuprous cyanide in N-methylpyrrolidinone under Rosenmund-von-Braun conditions. Compound "CF" is esterified by reaction with bromacetyl acetate using NaH as a base and THF as solvent to form compound "CG". Compound "CG" is reacted with $ClSO_3H$ in $CH_2Cl_2$ to form compound CH, which is reacted with $NH(CH_2CH_2OH)_2$ in $CHCl_3$ to form the compound "CI" having a water solubilization group bound to its upper rim. Compound "CI" is reacted with $Me_4NOH$, THF—$H_2O$ to hydrolyze the esters and form compound "CJ". Compound "CJ" is reacted with $NaBH_4$ and $CoCl_2$ to form the compound "CK". Compound "CK" can then be reacted with a protein (such as an antibody) to bind the protein and form the compound "CL".

Figure 10B:
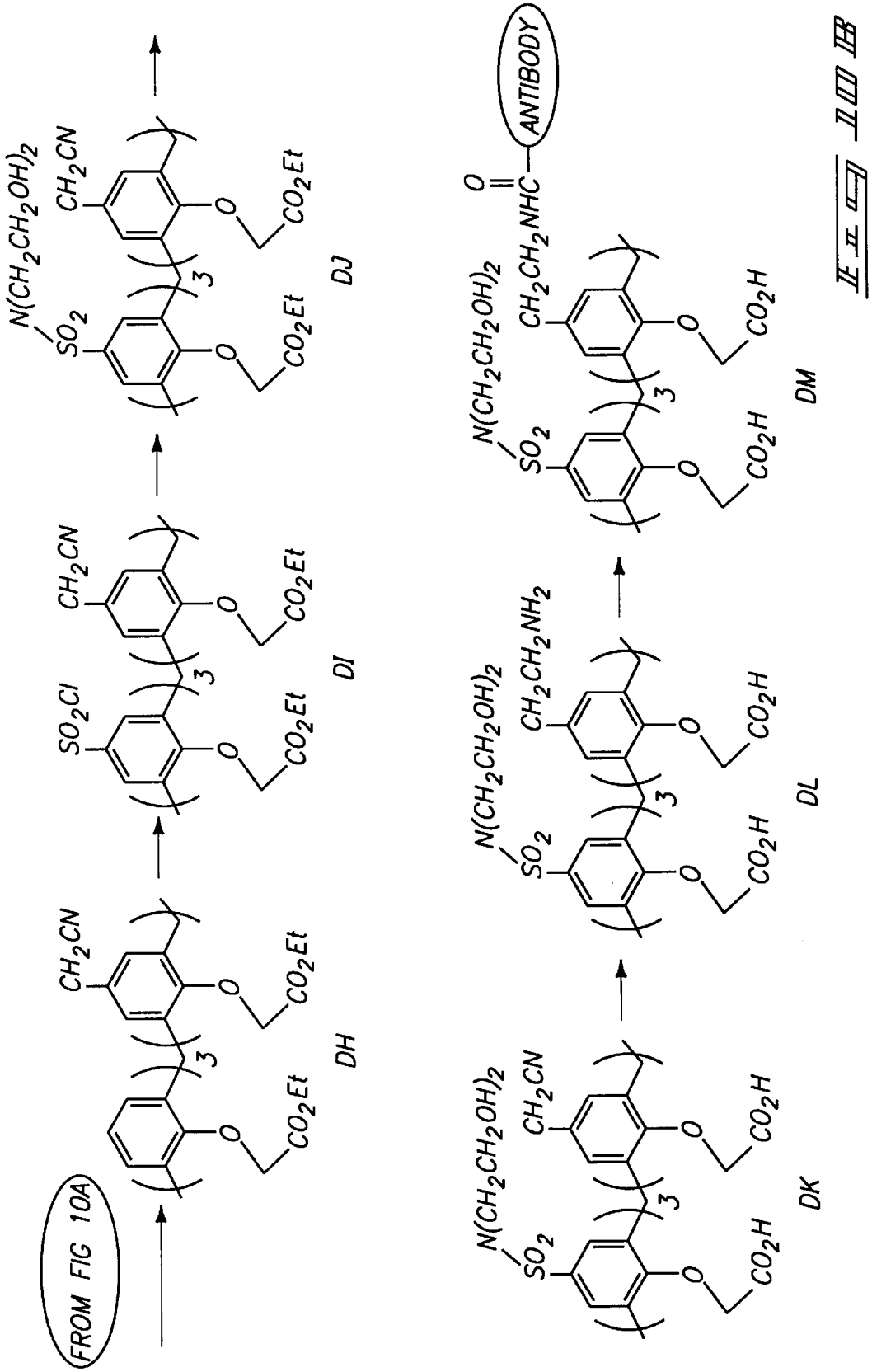
FIGS. 10A and B illustrate another series of methods for linking antibodies and water solubilization groups to compounds of the present invention.

Another process for forming a water solubilization group and a protein on an upper rim of a calixarene compound of the present invention is described with reference to FIGS. 10A and 10B. A starting material of t-butylcalix[4]arene (compound "DA") is reacted with benzoyl chloride utilizing 1-methylimidazole as a base to form a tribenzoylated derivative (compound "DB"). Compound "DB" is reacted with $AlCl_3$, phenol and toluene. Such results in Lewis acid catalyzed de-tert-butylation to form compound "DC". It is noted that the de-tert-butylation only occurs at the para position of the phenol hydroxy group, and that the para positions of the phenoxy ethers remain untouched. The benzoyl groups are de-protected by hydrolysis utilizing NaOH in EtOH—$H_2O$ to form compound "DD". Compound "DD" is then further derivatized by a chlormethylation procedure utilizing $ClCH_2OC_8H_{17}$ and $SnCl_4$ in $CH_2Cl_2$ to form compound "DE". Compound "DE" is reacted with NaCN in DMSO to form compound "DF". The remaining t-butyl groups of compound "DF" are removed using $AlCl_3$ as a Lewis acid catalyst in phenol and toluene to form the compound "DG". Compound "DG" is reacted with $BrCH_2COOEt$ and NaH in THF to form compound "DH". Compound "DH" is reacted with $ClSO_3H$ in $CH_2Cl_2$ to form compound "DI", which is then reacted with $NH(CH_2CH_2OH)_2$ in $CHCl_3$ to form compound "DJ". Compound "DJ" is reacted with $Me_4NOH$ in THF—$H_2O$ to form compound "DK", and compound "DK" is reacted with $NaBH_4$ and $CoCl_2$ to form compound "DL". Compound "DL" can then be attached to a protein (such as an antibody) to form compound "DM".

Figure 11:
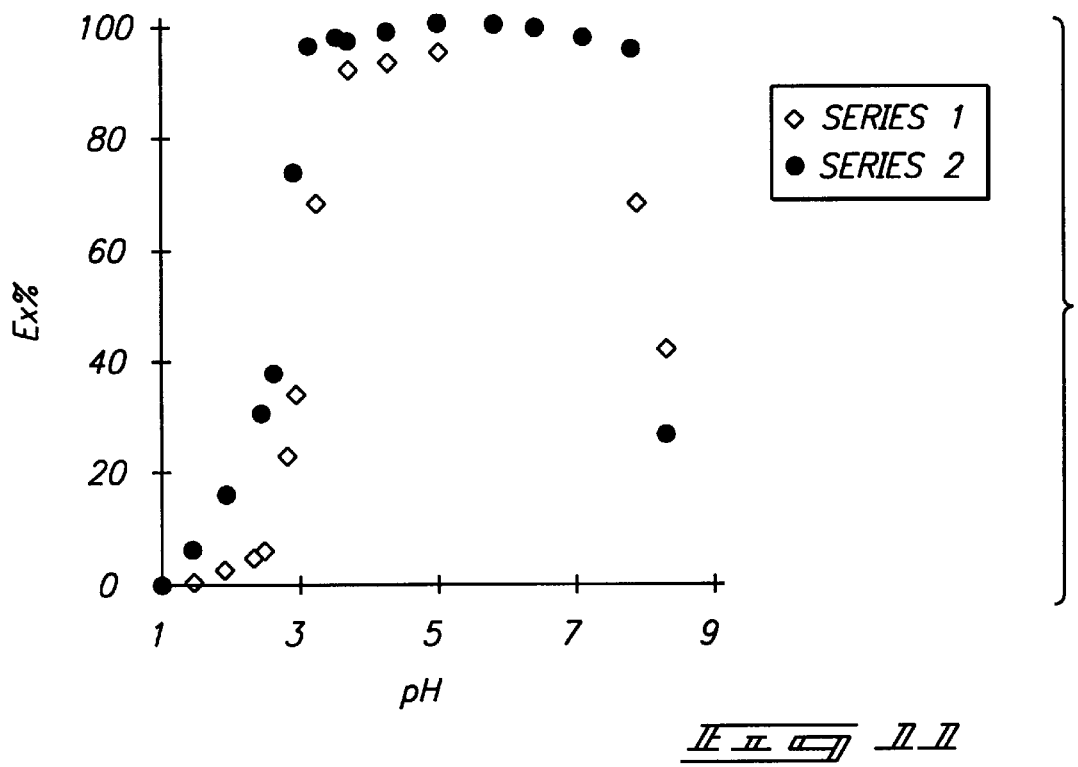
FIG. 11 shows a graph comparing pH dependence of Ac extraction for a pair of compounds of the present invention.

Competition experiments have been performed utilizing t-butyl-calix[4]arene-tetracarboxylic acid and t-butyl-calix[6]arene-hexacarboxylic acid. The experiments indicate that both t-butyl calix[4]arene-tetracarboxylic acid and t-butyl-calix[6]arene-hexacarboxylic acid are good ionophores for coordination of $Ac^{3+}$ under neutral or weakly acidic conditions. Specifically, two phase solvent extraction studies showed high selectivity of calix[4]arene-tetracarboxylic acid and calix[6]arene-hexacarboxylic acid for $Ac^{3+}$ over alkaline, alkaline earth, and zinc metal ions under neutral and weakly acidic conditions. The two phase solvent extraction experiments were carried out between water (1.5 mL, $[^{225}Ac]=10^{-3}$ mM) and chloroform (1.5 mL, [ionophore]=2 mM). The mixture was shaken for 30 minutes at 25° C. This time period was confirmed as being sufficient to achieve equilibrium within the mixture. The distribution ratio D ($[Ac^{3+}]$ in the organic phase/$[Ac^{3+}]$ in the aqueous phase) was measured with γ-ray spectrometry. Extractability (Ex %) was calculated as D/(1+D). FIG. 11 illustrates Ex % of $Ac^{3+}$ with calix[4]arene-tetracarboxylic acid and calix[6]arene-hexacarboxylic acid plotted against a pH of the aqueous phase. For calix[4]arene-tetracarboxylic acid, Ex % becomes appreciable at pH 2.0 and reaches a plateau at about pH 4.0, giving nearly 100% extractability. The Ex % decreases sharply at pH greater than 7.3. When pH reaches 8.0, only about 40% of $Ac^{3+}$ is extracted. The Ex % for calix[6]arene-hexacarboxylic acid shows a similar pH dependence. The Ex % increases from pH 1.5, reaches saturation at a pH of about 3.0, and decreases sharply after pH of about 7.5. The decrease in Ex % at higher pH can be explained by the formation of $Ac(OH)^{2+}$ species, which are probably too large to enter the rigid preorganized calixarene cavities.

Figure 12:
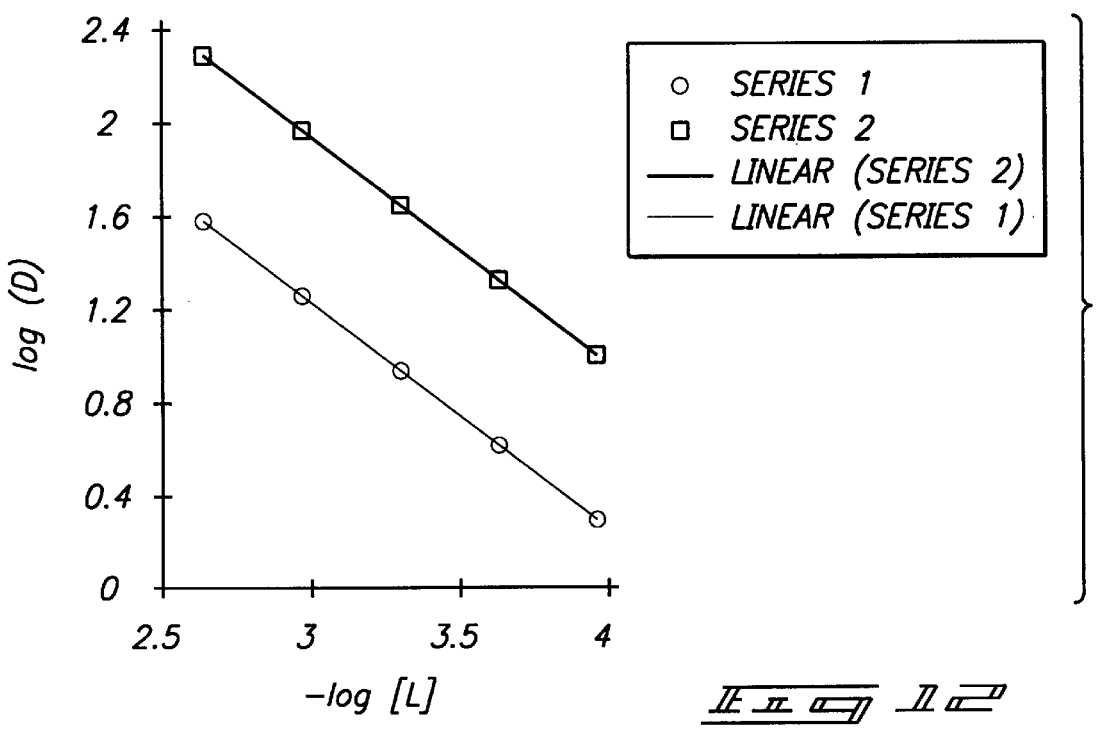
FIG. 12 shows a graph comparing concentration dependence of Ac extraction for a pair of compounds of the present invention.

Referring to FIG. 12, a plot of log(D) versus log[L] for the extraction of $Ac^{3+}$ by calix[4]arene-tetracarboxylic acid and calix[6]arene-hexacarboxylic acid at pH 6 is illustrated. [L] is the concentration of ligand, with ligand being either calix[4]arene-tetracarboxylic acid or calix[6]arene-hexacarboxylic acid. There is a linear relationship between log[L] and log(D) for both calix[4]arene-tetracarboxylic acid and calix[6]arene-hexacarboxylic acid. The slopes of log(D) vs. log[L] for both calix[4]arene-tetracarboxylic acid and calix[6]arene-hexacarboxylic acid are roughly equal to 1. Specifically, the data of the first series fits the equation y=−1.06x+5.114, with $R^2$=0.9991, and the data of the second series fits the equation y=−1.0467x+4.362, with $R^2$=0.9991. Such slopes approximately equal to 1 indicate that both calix[4]pg.25 arene-tetracarboxylic acid and calix[6]arene-hexacarboxylic acid form 1:1 complexes with $Ac^{3+}$ at pH 6.

As $^{225}Ac$ is radioactive, it is impossible to get the stability constant of the $^{225}Ac$ complex through common spectroscopic or potentiometric titration methods. Accordingly, a competition extraction method was utilized to ascertain relative extraction constants of $Ac^{3+}$ by calix[4]arene-tetracarboxylic acid and calix[6]arene-hexacarboxylic acid with respect to the water soluble ligand EDTA (ethylenediaminetetraacetic acid). The competition experiment was as follows. First, $^{225}Ac^{3+}$ (in water at pH 7) was extracted into a chloroform phase containing calix[4]arene-tetracarboxylic acid or calix[6]arene-hexacarboxylic acid. The organic base was then back-extracted with an aqueous phase containing EDTA at pH 7. A distribution ratio D was calculated as $[AcLH]_{org}/[AcEDTA]_{Aq}$, where L is either calix[4]arene-tetracarboxylic acid or calix[6]arene-hexacarboxylic acid, and where LH is a protonated form of either calix[4]arene-tetracarboxylic acid or calix[6]arene-hexacarboxylic acid.

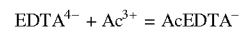

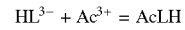

-continued $$K_1 = [\text{AcEDTA}]/[\text{EDTA}^{4-}][\text{Ac}^{3+}]$$

$$K_2 = [\text{AcLH}]/[\text{HL}^{3-}][\text{Ac}^{3+}]$$

$$K_2/K_1 = [\text{AcLH}][\text{EDTA}^{4-}]/[\text{AcEDTA}^-][\text{HL}^{3-}]$$

$$\text{Log}(K_2/K_1) = \log(D) + \log[\text{EDTA}^{4-}]/[\text{HL}^{3-}]$$

Figure 13:
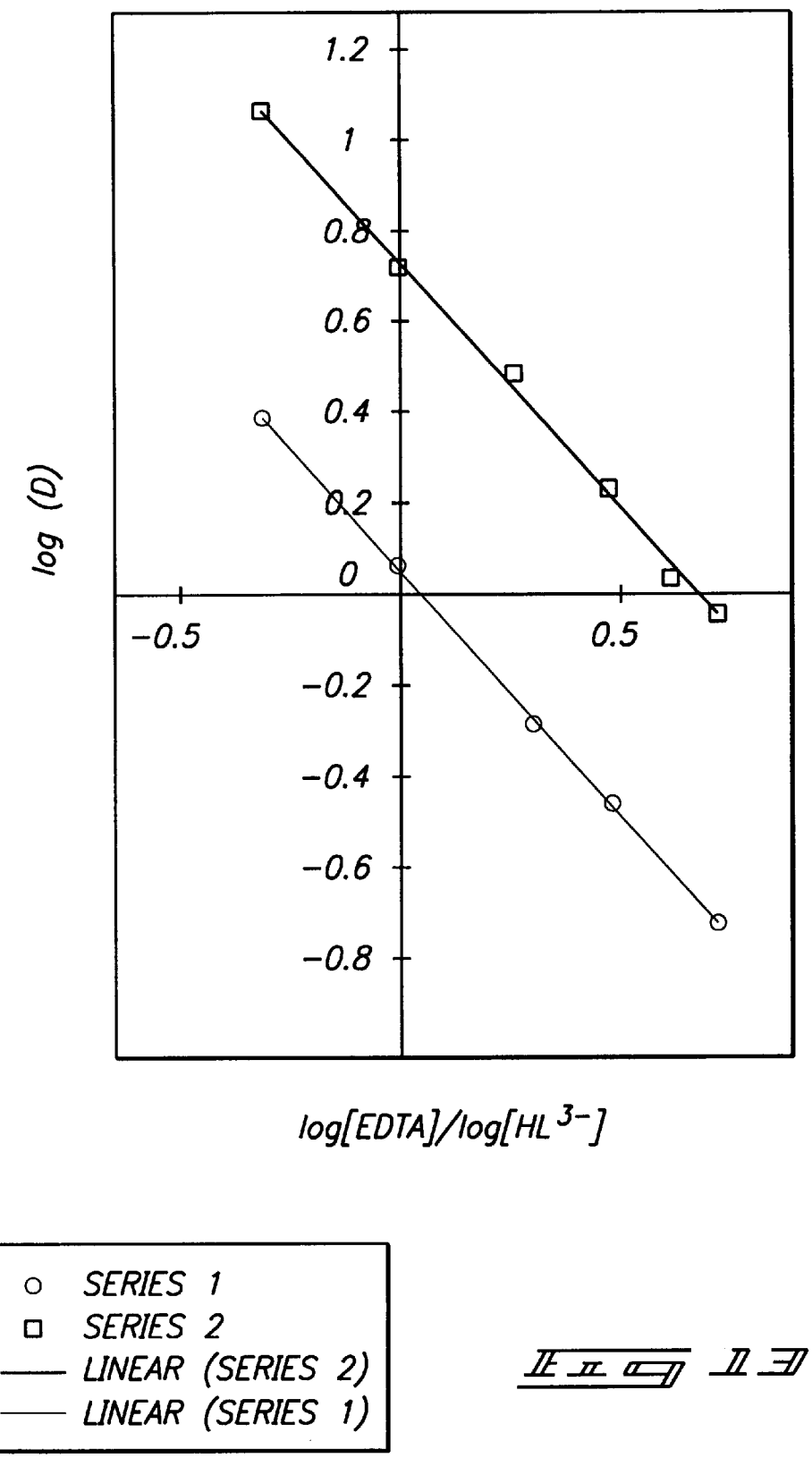
FIG. 13 shows a graph comparing Ac extraction in competition with EDTA for a pair of compounds of the present invention.

It is assumed that neither $\text{EDTA}^{4-}$ and $\text{AcEDTA}^-$ is soluble in a chloroform phase. The solubility of the $\text{HL}^{3-}$ and AcLH in the aqueous phase is neglected. A plot of $\log(D)$ versus $\log[\text{EDTA}^{4-}]/[\text{HL}^{3-}]$ is shown in FIG. 13. The plot has straight line slopes for both ligands of about 1, indicating that the above-described assumptions are good. (Specifically, the data of the first series fits the equation $y=-1.0411x+0.0472$, with $R^2=0.9981$, and the data of the second series fits the equation $y=-1.1317x+0.7616$, with $R^2=0.9925$.) From the intercepts of the slopes in FIG. 13, the extraction constants of the ligands calix[4]arene-tetracarboxylic acid and calix[6]arene-hexacarboxylic acid are determined relative to that of EDTA. Calix[4]arene-tetracarboxylic acid is determined to have a $K_2$ equal to 1.11 $K_1$, where $K_1$ is the extraction constant of Ac with EDTA. Calix[6]arene-hexacarboxylic acid is determined to have a $K_2$ equal to 5.75 $K_1$.

It was also investigated whether the $\text{Ac}^{3+}$ complexes with calix[4]arene-tetracarboxylic acid and calix[6]arene-hexacarboxylic acid were stable in the presence of high concentrations of alkaline, alkaline earth, and zinc metal ions. Aliquots of an organic phase containing the $^{225}\text{Ac}$ complexes were back-extracted with an aqueous solution containing a mixture of 10 mM each of $\text{Ca}^{2+}$, $\text{Mg}^{2+}$, $\text{Na}^+$, $\text{K}^+$, and $\text{Zn}^{2+}$ at pH 7.0. After shaking for five hours, calix[4]arene-tetracarboxylic acid shows no measurable loss of $\text{Ac}^{3+}$ from the organic phase to the aqueous phase. Further, calix[6]arene-hexacarboxylic acid shows a loss of only about 5% of $\text{Ac}^{3+}$ from the organic phase to the aqueous phase. The selective extraction of the trivalent $\text{Ac}^{3+}$ over the monovalent ions and divalent ions by the ligands calix[4] arene-tetracarboxylic acid and calix[6]arene-hexacarboxylic acid may be related to the high charge density of the $\text{Ac}^{3+}$ ion. The slightly poorer selectivity for $\text{Ac}^{3+}$ of calix[6]arene-hexacarboxylic acid relative to calix[4]arene-tetracarboxylic acid may be due to the calix[4]arene having a more rigid cavity than the larger cavity of calix[6]arene. Also, as the calix[6]arene-hexacarboxylic acid is more acidic than the calix[4]arene-tetracarboxylic acid, it can coordinate with alkaline earth metal ions at lower pH values.

The above experiments indicate that the calix[n]arene-carboxylic acids of the present invention can bind and retain $\text{Ac}^{3+}$ at physiological pHs. Further, the experiments indicate that calix[n]arene-carboxylic acids of the present invention can bind and retain $\text{Ac}^{3+}$ in environments containing a number of ions and salts, such as in vivo in biological systems. Accordingly, the calix[n]arene-carboxylic acids of the present invention are well suited for in vivo delivery of $\text{Ac}^{3+}$ to target destinations, such as cancer cells. The above experiments also suggest that calix[n]arene compounds derivatized with other ionizable groups besides carboxylic acids, such as, for example, hydroxamic acids, can also selectively bind $\text{Ac}^{3+}$ under physiological conditions.

Figure 14:
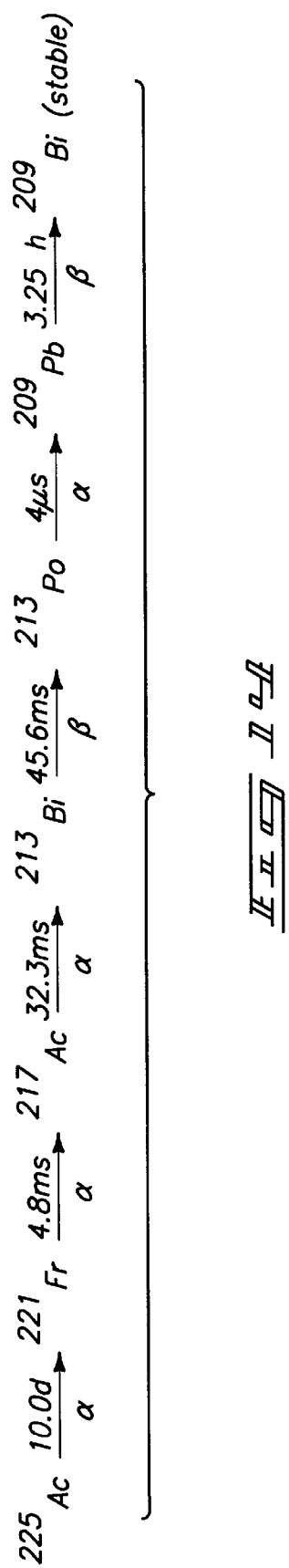
FIG. 14 illustrates a decay series for $^{225}$Ac.

For treatments of cancer, $^{225}\text{Ac}$ is a particularly effective radionuclide because $^{225}\text{Ac}$ generates alpha particles during its decay series to $^{209}\text{Bi}$(stable). Alpha particles are generally more lethal to cells than beta particles (electrons), X-rays, or gamma rays generated by radioactive processes, and so are preferred particles for killing cancer cells. A decay scheme for Ac-225 is shown in FIG. 14. The decay scheme shows that $^{225}\text{Ac}$ generates four alpha particles during its decay to $^{209}\text{Bi}$.

Ac-225 has an optimum physical half life for in vivo treatment of cancer. Specifically, the physical half life of Ac-225 is about 10 days. Recent studies indicate that a relatively long physical half life (four to 12 days) of an alpha emitter is most desirable for in vivo cancer treatment. Specifically, recent dosimetry modeling by Rao and Howell showed that alpha emitters were preferable to beta emitters for therapy effectiveness, and that the optimum physical half life of the radionuclide is one to three times the biological retention half-time of a radiolabeled antibody in a tumor. (See, Rao and Howell, *Time-Dose Fractionation in Radioimmunotherapy: Implications to Selection of Radionuclides*, J. Nucl. Med. 34(5): 105 p (1993): and Rao and Howell, *Time-Dose Fractionation in Radioimmunotherapy: Implications for Selection Radionuclides*, J. Nucl. Med. 34: 1801–1810 (1993).) The pharmacokinetics of continuous protein uptake in some targeted solid tumors extend over periods of time and the biological retention half-times of some antibodies in tumors may be long (four to six days). Typical tumor retention half-times are 48 to 96 hours (two to four days), and therefore optimal physical half-lives are two to 12 days, with longer half-times being preferred over shorter half-times.

In compliance with the statute, the invention has been described in language more or less specific as to structural and methodical features. It is to be understood, however, that the invention is not limited to the specific features shown and described, since the means herein disclosed comprise preferred forms of putting the invention into effect. The invention is, therefore, claimed in any of its forms or modifications within the proper scope of the appended claims appropriately interpreted in accordance with the doctrine of equivalents.

What is claimed is:

1. A compound comprising:
    a calix[n]arene group, wherein n is an integer greater than 3, the calix[n]arene group comprising an upper rim and a lower rim;
    at least one ionizable group attached to the lower rim; and
    a radionuclide ion selected from the group consisting of lanthanide elements bound to the ionizable group.

2. The compound of claim 1 wherein n is less than 7.

3. The compound of claim 1 wherein the ion is an imaging agent selected from the group consisting of $\text{Eu}^{2+}$, $\text{Tb}^{4+}$ and $\text{Yb}^{2+}$.

4. The compound of claim 1 wherein the at least one ionizable group comprises one or more functional groups selected from the group consisting of carboxylic acid and hydroxamic acid.

5. A compound comprising:
    a calix[n]arene group, wherein n is an integer greater than 3, the calix[n]arene group comprising an upper rim and a lower rim;
    at least one ionizable group attached to the lower rim;
    a radionuclide ion bound to the ionizable group; and
    a linking group attached to the upper rim, the linking group being configured to covalently attach the compound to a protein.

6. The compound of claim 1 further comprising a linking group attached to the upper rim, the linking group comprising one or more functional groups selected from the group consisting of amines, halogens, and aldehydes.

7. The compound of claim 1 further comprising at least one water solubilization group attached to the upper rim.

8. The compound of claim 1 further comprising at least one water solubilization group selected from the group consisting of sulfonates, nitrates, carboxylates and ammonium ions attached to the upper rim.

9. A compound comprising:
a calix[n]arene group wherein n is an integer greater than 3, the calix[n]arene group comprising an upper rim and a lower rim;
at least one ionizable group attached to the lower rim;
an ion bound to the ionizable group; and
a (2-hydroxyethyl)aminosulfonyl functional group attached to the upper rim.

10. The compound of claim 1 further comprising:
a linking group attached to the upper rim, the linking group comprising one or more functional groups selected from the group consisting of amines, halogens, and aldehydes; and
at least one water solubilization group attached to the upper rim, the water solubilization group being selected from the group consisting of sulfonates, nitrates, carboxylates and ammonium ions.

11. A method of making a radionuclide complexing compound, comprising:
providing a calix[n]arene compound, wherein n is an integer greater than 3, the calix[n]arene compound comprising at least one phenolic hydroxyl group;
converting the hydroxyl group to an ester;
converting the ester to an acid; and
providing a radionuclide selected from the group consisting of lanthanide elements bound to the acid.

12. The method of claim 11 wherein the calix[n]arene compound comprises more than one phenolic hydroxyl groups and wherein less than all of the phenolic hydroxyl groups are converted to esters.

13. The method of claim 11 wherein the acid comprises an acid selected from the group consisting of carboxylic acid and hydroxamic acid.

14. The method of claim 11 wherein the ester is converted to a carboxylic acid, and wherein the carboxylic acid is converted to a hydroxamic acid.

15. A method of making a radionuclide complexing compound, comprising:
providing a calix[n]arene compound, wherein n is an integer greater than 3, the calix[n]arene compound comprising an upper rim, a lower rim, and at least one phenolic hydroxyl group attached to the lower rim;
converting the hydroxyl group to an ester;
converting the ester to an acid;
forming one or more linking groups attached to the upper rim, the linking groups being configured to covalently attach the calix[n]arene compound to a protein; and
providing a radionuclide bound to the acid.

16. The compound of claim 15 further comprising at least one water solubilization group attached to the upper rim.

17. The compound of claim 15 further comprising at least one water solubilization group selected from the group consisting of sulfonates, nitrates, carboxylates and ammonium ions attached to the upper rim.

18. The compound of claim 15 further comprising a (2-hydroxyethyl)aminosulfonyl functional group attached to the upper rim.

19. The method of claim 11 wherein the calix[n]arene comprises an upper rim and a lower rim, the acid being attached to the lower rim, the method further comprising:
forming a linking group attached to the upper rim, the linking group comprising a nitrate group; and
converting the nitrate group to an amine.

20. A method of making a radionuclide complexing compound, comprising:
providing a calix[n]arene compound, wherein n is an integer greater than 3, the calix[n]arene compound comprising at least one phenolic hydroxyl group, an upper rim, and a lower rim;
converting the hydroxyl group to an ester;
forming a linking group attached to the upper rim, the linking group comprising a nitrate group;
converting the ester to an acid;
converting the nitrate group to an amine;
covalently attaching the amine to a protein; and
providing a radionuclide bound to the acid.

21. The method of claim 20 wherein the covalently attaching the amine to a protein occurs before providing the radionuclide bound to the acid.

22. The method of claim 20 wherein the covalently attaching the amine to a protein occurs after providing the radionuclide bound to the acid.

23. The method of claim 20 wherein the acid is attached to the lower rim, wherein the ester is converted to a carboxylic acid, and wherein the carboxylic acid is converted to a hydroxamic acid.

24. A method of making a radionuclide complexing compound, comprising:
providing a calix[n]arene compound, wherein n is an integer greater than 3, the calix[n]arene compound comprising at least one phenolic hydroxyl group, an upper rim, and a lower rim;
converting the hydroxyl group to an ester;
forming a linking group attached to the upper rim, the linking group comprising an aldehyde group;
converting the ester to an acid;
covalently attaching the calix[n]arene to a protein by reacting an amino group from the protein with the aldehyde group; and
providing a radionuclide bound to the acid.

25. The method of claim 20 wherein the ester is converted to a carboxylic acid, and wherein the carboxylic acid is converted to a hydroxamic acid, the acid being attached to the lower rim.

26. A method of making a radionuclide complexing compound, comprising:
providing a calix[n]arene compound, wherein n is an integer greater than 3, the calix[n]arene compound comprising at least one phenolic hydroxyl group, an upper rim, and a lower rim;
converting the hydroxyl group to an ester;
forming a bromine attached to the upper rim;
converting the ester to an acid;
covalently attaching the calix[n]arene to a protein by displacing the bromine with an amino group from the protein; and
providing a radionuclide bound to the acid.

27. The method of claim 26 wherein the acid is attached to the lower rim, wherein the ester is converted to a carboxylic acid, and wherein the carboxylic acid is converted to a hydroxamic acid.

28. A method of extracting a radionuclide, comprising:
providing a sample comprising an $Ac^{3+}$ radionuclide;

providing a calix[n]arene compound in contact with the sample, wherein the calix[n]arene compound is configured to selectively bind $Ac^{3+}$, and comprises one or more compounds selected from the group consisting of calix[4]arene-monocarboxylic acid, calix[4]arene-dicarboxylic acid, calix[4]arene-tricarboxylic acid, calix[4]arene-tetracarboxylic acid, calix[4]arene-monohydroxamic acid, calix[4]arene-dihydroxamic acid, calix[4]arene-trihydroxamic acid, calix[4]arene-tetrahydroxamic acid, calix[6]arene-monocarboxylic acid, calix[6]arene-dicarboxylic acid, calix[6]arene-tricarboxylic acid, calix[6]arene-tetracarboxylic acid, calix[6]arene-pentacarboxylic acid, calix[6]arene-hexacarboxylic acid, calix[6] arene-monohydroxamic acid, calix[6]arene-dihydroxamic acid, calix[6] arene-trihydroxamic acid, calix[6]arene-tetrahydroxamic acid, calix[6]arene-pentahydroxamic acid and calix[6] arene-hexahydroxamic acid; and extracting radionuclide from the sample into the calix[n] arene compound.

29. A method of delivering a radionuclide to a target location, comprising:

providing a calix[n]arene compound, wherein n is an integer greater than 3, the calix[n]arene compound comprising at least one ionizable group;

providing a radionuclide bound to the calix[n]arene compound through the at least one ionizable group; and providing an antibody attached to the calix[n]arene compound, the antibody being specific for the target location.

30. The method of claim 29 wherein the at least one ionizable group comprises one or more functional groups selected from the group consisting of carboxylic acid and hydroxamic acid.

31. The method of claim 29 wherein the antibody comprises a nitrogen, and wherein the calix[n]arene compound is attached to the antibody through a covalent bond to the nitrogen.

32. The method of claim 29 wherein the calix[n]arene compound is configured to selectively bind $Ac^{3+}$, and wherein the radionuclide comprises $Ac^{3+}$.

33. The method of claim 29 wherein the calix[n]arene comprises an upper rim and a lower rim, and wherein the at least one ionizable group is attached to the lower rim, the compound further comprising at least one water solubilization group attached to the upper rim.

34. The method of claim 29 wherein the calix[n]arene comprises an upper rim and a lower rim, and wherein the at least one ionizable group is attached to the lower rim, the compound further comprising at least one water solubilization group selected from the group consisting of sulfonates, nitrates, carboxylates and ammonium ions attached to the upper rim.

35. The method of claim 29 wherein the calix[n]arene comprises an upper rim and a lower rim, and wherein the at least one ionizable group is attached to the lower rim, the compound further comprising a (2-hydroxyethyl) aminosulfonyl functional group attached to the upper rim.

36. The method of claim 29 wherein the target location is a cancer cell.

37. The compound of claim 1 wherein the at least one ionizable group comprises one or more functional groups having alkyl chain lengths of only three carbons or less.

38. The method of claim 16 wherein the acid has an alkyl chain length of only three carbons or less.

* * * * *